United States Patent
Mizushima et al.

(10) Patent No.: US 12,098,129 B2
(45) Date of Patent: Sep. 24, 2024

(54) PHARMACEUTICAL COMPOSITION FOR TREATING FIBROSIS

(71) Applicants: LTT BIO-PHARMA CO., LTD., Minato-ku (JP); MUSASHINO UNIVERSITY, Koto-ku (JP)

(72) Inventors: Tohru Mizushima, Minato-ku (JP); Ken-ichiro Tanaka, Nishitokyo (JP)

(73) Assignees: LTT BIO-PHARMA CO., LTD., Minato-ku (JP); MUSASHINO UNIVERSITY, Koto-ku (JP)

( * ) Notice: Subject to any disclaimer, the term of this patent is extended or adjusted under 35 U.S.C. 154(b) by 775 days.

(21) Appl. No.: 17/270,304

(22) PCT Filed: Sep. 26, 2019

(86) PCT No.: PCT/JP2019/037947
§ 371 (c)(1),
(2) Date: Feb. 22, 2021

(87) PCT Pub. No.: WO2020/067333
PCT Pub. Date: Apr. 2, 2020

(65) Prior Publication Data
US 2021/0198199 A1    Jul. 1, 2021

(30) Foreign Application Priority Data
Sep. 27, 2018   (JP) ................................ 2018-182817

(51) Int. Cl.
| | | |
|---|---|---|
| C07D 211/14 | (2006.01) | |
| A61K 9/00 | (2006.01) | |
| A61P 11/00 | (2006.01) | |
| C07C 50/28 | (2006.01) | |

(52) U.S. Cl.
CPC .......... C07D 211/14 (2013.01); A61K 9/0053 (2013.01); A61K 9/007 (2013.01); A61P 11/00 (2018.01); C07C 50/28 (2013.01)

(58) Field of Classification Search
CPC .............. A61K 31/4453; A61K 31/122; A61K 31/397; A61K 31/40; A61K 31/55; A61P 1/16; A61P 13/12
See application file for complete search history.

(56) References Cited

U.S. PATENT DOCUMENTS

| | | | |
|---|---|---|---|
| 4,514,420 A * | 4/1985 | Imada .................... | A61K 31/12 514/532 |
| 4,526,719 A | 7/1985 | Terao et al. | |
| 2006/0199841 A1* | 9/2006 | Tihanyi ................... | A61P 21/02 514/317 |
| 2010/0129431 A1* | 5/2010 | Schwarz ................. | A61P 31/00 514/678 |
| 2010/0298329 A1 | 11/2010 | Shaw et al. | |

FOREIGN PATENT DOCUMENTS

| | | |
|---|---|---|
| JP | 58-177934 A | 10/1983 |
| WO | WO 2009/038771 A2 | 3/2009 |

OTHER PUBLICATIONS

Tanaka, Ki., Niino, T., Ishihara, T. et al. Protective and therapeutic effect of felodipine against bleomycin-induced pulmonary fibrosis in mice. Sci Rep 7, 3439 (2017). (Year: 2017).*
Jiang, L., Li, Y., Yu, J. et al. A dry powder inhalable formulation of salvianolic acids for the treatment of pulmonary fibrosis: safety, lung deposition, and pharmacokinetic study. Drug Deliv. and Transl. Res. 11, 1958-1968 (2021). (Year: 2021).*
Khalil W., et al. Am J Respir Cell Mol Biol. Sep. 2015;53(3):391-9. (Year: 2015).*
Partial Supplementary European Search Report issued May 24, 2022 in European Patent Application No. 19867505.0, 12 pages.
Sugizaki, T., et al. "Idebenone has preventative and therapeutic effects on pulmonary fibrosis via preferential suppression of fibroblast activity", Cell Death Discovery, vol. 5, No. 1, Nov. 18, 2019, p. 146 (pp. 1-15), XP055920053.
European Office Action issued Feb. 19, 2024 in European Patent Application No. 19 867 505.0, 8 pages.
Tanaka et al., "Therapeutic Effects of Eperisone on Pulmonary Fibrosis via preferential suppression of fibroblast activity", Cell Death Discovery, vol. 8, No. 1, Article No. 52, Feb. 8, 2022, 9 pages, XP93130410.

(Continued)

*Primary Examiner* — Matthew P Coughlin
*Assistant Examiner* — Quincy A Mckoy
(74) *Attorney, Agent, or Firm* — Oblon, McClelland, Maier & Neustadt, L.L.P.

(57) ABSTRACT

To provide a novel therapeutic agent for fibrosis that induces selective cell death of lung fibroblasts and suppresses lung fibrosis without injuring alvocar epithelial cells.
A pharmaceutical composition for treating fibrosis, the pharmaceutical composition comprising a compound of formula (I) or formula (II):

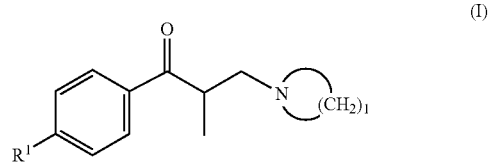

(I)

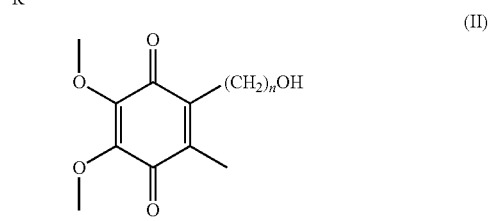

(II)

wherein in formula (I), $R^1$ represents a $C_{1-4}$ alkyl group optionally substituted with a halogen atom, and l represents an integer of 3 to 6; and in formula (II), n represents an integer of 8 to 12,
or a pharmaceutically acceptable salt thereof or a solvate of the compound or the salt thereof.

6 Claims, 32 Drawing Sheets

(56) References Cited

OTHER PUBLICATIONS

International Search Report issued on Dec. 24, 2019 in PCT/JP2019/037947 filed on Sep. 26, 2019, 2 pages.
Raghu, G. et al., "An Official ATS/ERS/JRS/ALAT Clinical Practice Guideline: Treatment of Idiopathic Pulmonary Fibrosis," American Journal of Respiratory and Critical Care Medicine, vol. 192, No. 2, 2015, pp. e3-e19.
Noble, P. W. et al., "Pirfenidone in patients with idiopathic pulmonary fibrosis (Capacity): two randomised trials," Lancet, vol. 377, 2011, pp. 1760-1769.
Richeldi, L. et al., "Efficacy and Safety of Nintedanib in Idiopathic Pulmonary Fibrosis," The New England Journal of Medicine, vol. 370, No. 22, 2014, pp. 2071-2082.
Hinz, B. et al., "Biological Perspectives The Myofibroblast *One Function*, Multiple Origins," The American Journal of Pathology, vol. 170, No. 6, 2007, pp. 1807-1816.
Phan, S. H., "The Myofibroblast in Pulmonary Fibrosis," Chest, vol. 122, No. 6, 2002, pp. 286S-289S.
Scotton, C. J. et al., "Molecular Targets in Pulmonary Fibrosis The Myofibroblast in Focus," Chest, vol. 132, No. 4, 2007, pp. 1311-1321.
Li, J. et al., "Transforming growth factor β regulates β-catenin expression in lung fibroblast through NF-κB dependent pathway," International Journal of Molecular Medicine, vol. 34, 2014, pp. 1219-1224.
Jarman, E. R. et al., "A translational preclinical model of interstitial pulmonary fibrosis and pulmonary hypertension: mechanistic pathways driving disease pathophysiology," Physiological Reports, vol. 2, Iss. 9, e12133, 2014, pp. 1-19.
Kisseleva, T. et al., "Fibrogenesis of Parenchymal Organs," Proceedings of The American Thoracic Society, vol. 5, 2008, pp. 338-342.
Willis, B. C. et al., "TGF-β-induced EMT: mechanisms and implications for fibrotic lung disease," Am. J. Physiol. Lung Cell Mol. Physiol., vol. 293, 2007, pp. L525-L534.
Kasai, H et al., "TGF-β1 induces human alveolar epithelial to mesenchymal cell transition (EMT)," Respiratory Research, vol. 6, No. 56, 2005, pp. 1-15.
Conte, E. et al., "Effect of pirfenidone on proliferation, TGF-β-induced myofibroblast differentiation and fibrogenic activity of primary human lung fibroblasts," European Journal of Pharmaceutical Sciences, vol. 58, 2014, pp. 13-19.
Hisatomi, K. et al., "Pirfenidone inhibits TGF-β1-induced overexpression of collagen type I and heat shock protein 47 in A549 cells," BMC Pulmonary Medicine, vol. 12, No. 24, 2012, pp. 1-9.
Wollin, L. et al., "Antifibrotic and Anti-inflammatory Activity of the Tyrosine Kinase Inhibitor Nintedanib in Experimental Models of Lung Fibrosis," J. Pharmacol. Exp. Ther., vol. 349, 2014, pp. 209-220.
Mizuno, K. et al., "P-52 Study on the effect of epelisone hydrochloride in the chronic respiratory diseases," Journal of the Japanese Respiratory Society, vol. 41, P-52, 2003, p. 127, 5 total pages (with English translation).
Hasegawa, M. et al., "Characteristics of pathophysiology in COPD," Japanese Journal of Clinical Medicine, vol. 65, No. 4, 2007, pp. 639-643 (with English abstract).
Sato, Y., "A Study on the Diffusion of Idebenone into Skeletal Muscle," Clinical Report, vol. 26, No. 6, 1992, 4 total pages (with partial English translation).
Betsuyaku, T., "Mechanism of the Development of Pulmonary Emphysema," Connective Tissue, vol. 34, 2002, pp. 235-245 (with English abstract).
Jauslin, M. L. et al., "Protective effects of Fe-Aox29, a novel antioxidant derived from a molecular combination of Idebenone and vitamin E, in immortalized fibroblasts and fibroblasts from patients with Friedreich Ataxia," Mol. Cell. Biochem., vol. 302, 2007, pp. 79-85.
Momomura. S.-I., "3. Fibrosis of the Viscera and its Treatment, 4) Cardiac Fibrosis and Its Treatment," Nihon Naika Gakkai Zasshi, vol. 103, No. 9, 2014, pp. 2188-2192.
Abdelazim, S. A. et al., "Potential Antifibrotic and Angiostatic Impact of Idebenone, Carnosine and Vitamin E in Nano-Sized Titanium Dioxide-Induced Liver Injury," Cell. Physiol. Biochem., vol. 35, 2015, pp. 2402-2411.

\* cited by examiner

PHARMACEUTICAL COMPOSITION FOR TREATING FIBROSIS

CROSS REFERENCE TO RELATED APPLICATIONS

This application is a 371 of International Patent Application No. PCT/JP2019/037947, filed on Sep. 26, 2019, and claims priority to Japanese Patent Application No. 2018-182817, filed on Sep. 27, 2018, both of which are incorporated herein by reference in their entireties.

TECHNICAL FIELD

The present invention relates to a pharmaceutical composition for treating fibrosis.

BACKGROUND ART

Idiopathic pulmonary fibrosis (IPF) is a refractory disease with poor prognosis, and is associated with a very low median survival time of from 2.8 to 4.2 years after diagnosis. Steroids and immunosuppressive agents have been heretofore used as therapeutic drugs for IPF, and reported to be not effective in large scale clinical trials. In recent years, two new drugs, pirfenidone and nintedanib, have been launched in the market as antifibrotic drugs. These drugs have been shown to suppress a decrease in forced vital capacity (FVC) of IPF patients in clinical trials (Non-Patent Literatures 1 to 3), but the efficacy of long-term use of these drugs has not been revealed. Both of the drugs are known to pose problem of causing severe side effects, particularly gastrointestinal disorder (Non-Patent Literatures 2 and 3). Therefore, it is very important to develop a novel IPF therapeutic drug with higher safety and efficacy.

Though the mechanisms of onset and exacerbation of IPF have not been revealed, the main cause of IPF may be injury of alveolar epithelial cells by various stimuli, which triggers abnormal proliferation and activation of lung fibroblast cells (Non-Patent Literatures 4 to 6). Specifically, it has been reported that in the lung tissues of IPF patients, myofibroblast cells are increased in number and accumulated as a result of activation of fibroblast cells (Non-Patent Literature 7). It has been reported that in animal IPF models, myofibroblast cells are expanded and accumulated as in humans (Non-Patent Literature 8). It is considered that as a result, extracellular matrixes such as collagen are unusually produced and accumulated, and thus abnormal repair and remodeling proceed, so that the lung becomes fibrotic.

Some origins of myofibroblast cells have been reported, and the myofibroblast cells are classified broadly into those that differentiate from fibroblast cells and those that differentiate from epithelial-mesenchymal transition (EMT). Specifically, it has been reported that when a stimulus such as transforming growth factor (TGF)-β1 acts on fibroblast cells, the fibroblast cells differentiate into myofibroblast cells (Non-Patent Literature 9). Further, it has become evident that when TGF-β1 acts on alveolar epithelial cells, epithelial-mesenchymal transition is induced, so that the alveolar epithelial cells are transformed into myofibroblast cells (Non-Patent Literatures 10 and 11). Therefore, compounds which suppress induction of alveolar epithelial cells into myofibroblast cells or suppress collagen production of fibroblast cells without injuring alveolar epithelial cells may serve as good therapeutic drugs for IPF. In fact, pirfenidone and nintedanib launched in the market recently have been reported to suppress differentiation of fibroblast cells into myofibroblast cells, EMT of alveolar epithelial cells, and collagen production by activated fibroblast cells (Non-Patent Literatures 12 to 14).

CITATIONS

Non-Patent Literatures

[Non-Patent Literature 1] Am. J. Respir. Crit. Care Med. 192, e3-e19(2015)
[Non-Patent Literature 2] Lancet 377, 1760-1769(2011)
[Non-Patent Literature 3] N. Engl. J. Med. 370, 2071-2082 (2014)
[Non-Patent Literature 4] Am. J. Pathol. 170, 1807-1816 (2007)
[Non-Patent Literature 5] Chest 122, 286S-289S(2002)
[Non-Patent Literature 6] Chest 132, 1311-1321(2007)
[Non-Patent Literature 7] Int. J. Mol. Med. 34, 1219-1224 (2014)
[Non-Patent Literature 8] Physiol. Rep. 2, (2014)
[Non-Patent Literature 9] Proc. Am. Thorac. Soc. 5, 338-342 (2008)
[Non-Patent Literature 10] Am. J. Physiol. Lung Cell Mol. Physiol 293, L525-534(2007)
[Non-Patent Literature 11] Respir Res. 6, 56(2005)
[Non-Patent Literature 12] Eur. J. Pharm. Sci. 58, 13-19 (2014)
[Non-Patent Literature 13] BMC Pulm Med. 12, 24(2012)
[Non-Patent Literature 14] J. Pharmacol. Exp. Ther. 349, 209-220(2014)

SUMMARY OF THE INVENTION

Problem to be Solved

The present invention aims to provide a novel therapeutic agent for fibrosis that induces selective cell death of lung fibroblasts and suppresses pulmonary fibrosing without injuring alveolar epithelial cells.

Solution to the Problem

As a result of various attempts to find a drug having the above effects among existing approved drugs whose safety on human was sufficiently confirmed, the present inventors found that the compound of formula (I) or (II) below selectively show activity on fibroblasts and have an excellent effect of suppressing fibrosing in vivo, to complete the present invention.

The present invention provides the following [1] to [14].

[1] A pharmaceutical composition for treating fibrosis, the pharmaceutical composition comprising a compound of formula (I) or formula (II):

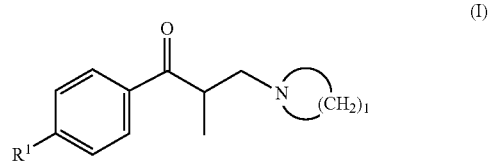

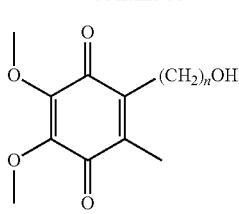

(II)

wherein in formula (I), $R^1$ represents a $C_{1-4}$ alkyl group optionally substituted with a halogen atom, and l represents an integer of 3 to 6; and in formula (II), n represents an integer of 8 to 12,
or a pharmaceutically acceptable salt thereof or a solvate of the compound or the salt thereof.

[2] The pharmaceutical composition according to [1], comprising a compound of formula (I), or a pharmaceutically acceptable salt thereof or a solvate of the compound or the salt thereof.

[3] The pharmaceutical composition according to [2], wherein in formula (I), l is 4 or 5, and $R^1$ is a methyl group, an ethyl group or a trifluoromethyl group.

[4] The pharmaceutical composition according to [2] or [3], wherein in formula (I), l is 5, and $R^1$ is a methyl group or an ethyl group

[5] The pharmaceutical composition according to [1], comprising a compound of formula (II), or a pharmaceutically acceptable salt thereof or a solvate of the compound or the salt thereof.

[6] The pharmaceutical composition according to [5], wherein in formula (II), n is 10.

[7] The pharmaceutical composition according to any one of [1] to [6], wherein the fibrosis is a pulmonary fibrosis.

[8] The pharmaceutical composition according to [7], wherein the pulmonary fibrosis is idiopathic pulmonary fibrosis.

[9] The pharmaceutical composition according to any one of [1] to [8], wherein the pharmaceutical composition is formulated for airway administration.

[10] The pharmaceutical composition according to any one of [1] to [8], wherein the pharmaceutical composition is formulated for oral administration.

[11] The pharmaceutical composition according to any one of [1] to [8], wherein the pharmaceutical composition is formulated for transveous administration.

[12] A compound of formula (I) or formula (II):

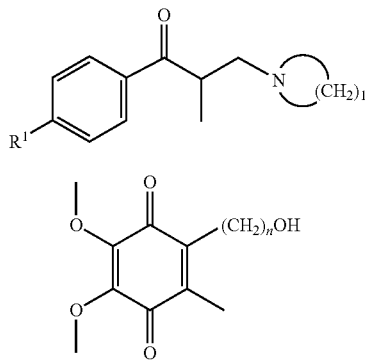

wherein in formula (I), $R^1$ represents a $C_{1-4}$ alkyl group optionally substituted with a halogen atom, and l represents an integer of 3 to 6; and in formula (II), n represents an integer of 8 to 12, or a pharmaceutically acceptable salt thereof or a solvate of the compound or the salt thereof, for use in treating fibrosis, the compound.

[13] Use of a compound of formula (I) or formula (II):

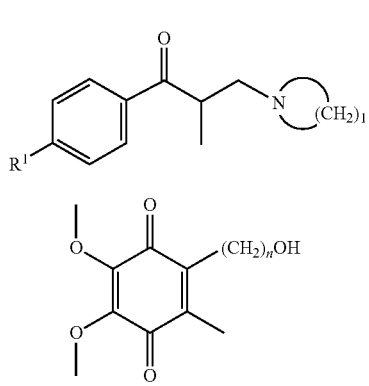

wherein in formula (I), $R^1$ represents a $C_{1-4}$ alkyl group optionally substituted with a halogen atom, and l represents an integer of 3 to 6; and in formula (II), n represents an integer of 8 to 12, or a pharmaceutically acceptable salt thereof or a solvate of the compound or the salt thereof, in the manufacture of a pharmaceutical composition for the treatment of fibrosis.

[14] A method for treating fibrosis, the method comprising administering an effective amount of a compound of formula (I) or formula (II):

(I)

(II)

wherein in formula (I), $R^1$ represents a $C_{1-4}$ alkyl group optionally substituted with a halogen atom, and l represents an integer of 3 to 6; and in formula (II), n represents an integer of 8 to 12, or a pharmaceutically acceptable salt thereof or a solvate of the compound or the salt thereof.

Advantageous Effect of the Invention

The compounds of formula (I) and formula (II) are compounds which have been used as pharmaceutical drugs, and whose safety was confirmed. These compounds show a selective cell death inducing action on lung fibroblast cells and an excellent pulmonary fibrosing suppressing action with a small dose not to injure alveolar epithelial cells, the effect is completely different from the effect conventionally known. Accordingly, such a compound is useful as a therapeutic drug for various fibroses, particularly idiopathic pulmonary fibrosis.

DESCRIPTION OF EMBODIMENTS

Figure 1A:
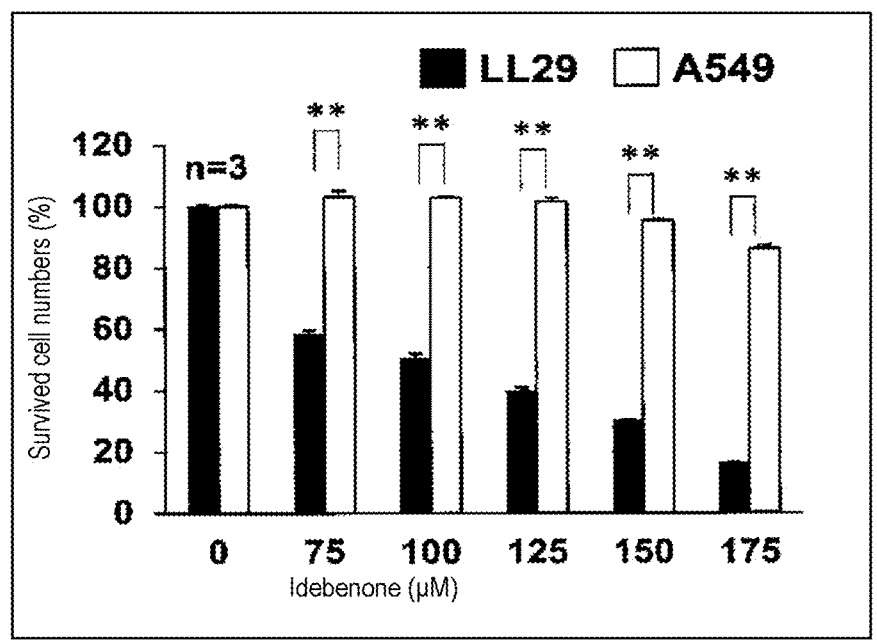
FIG. 1A shows an action of idebenone on the survived cell numbers (%) of LL29 cell and A549 cell.

An active ingredient contained in a pharmaceutical composition for treating fibrosis according to the present invention is a compound of formula (I) or formula (II):

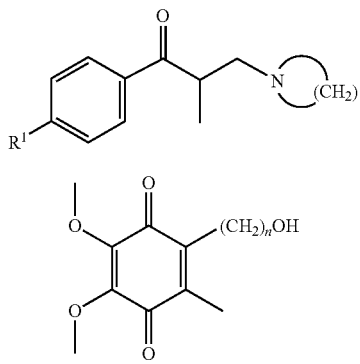

wherein in formula (I), $R^1$ represents a $C_{1-4}$ alkyl group optionally substituted with a halogen atom, and l represents an integer of 3 to 6; and in formula (II), n represents an integer of 8 to 12, or a pharmaceutically acceptable salt thereof or a solvate of the compound or the salt thereof.

The compound of formula (I) is a type of antispasmodic agent, and is known to act on both the central nervous system and the vascular smooth muscle to improve myotonia by relief of pain of the smooth muscle, improvement of ischemia and relaxation of tension and relax stiffness and spasticity. However, the action on fibrosis is not known at all. In particular, the compound of formula (I) has an effect of specifically inducing cell death on fibroblast cells, more preferably lung fibroblast cells. The compound of formula (I) has an effect of specifically suppressing activation of fibroblast cells, more preferably lung fibroblast cells. The compound of formula (I) has an effect of suppressing the fibrosing of tissues, particularly the fibrosing of lung tissues. The compound of formula (I) has an effect of suppressing a decrease in respiratory function. The compound of formula (I) has an effect of suppressing injury of tissues, particularly injury of lung tissues.

Examples of the $C_{1-4}$ alkyl group optionally substituted with a halogen atom as $R^1$ in formula (I) include $C_{1-4}$ alkyl groups optionally substituted with 1 to 3 chlorine atoms, fluorine atoms, bromine atoms or iodine atoms. Specific examples thereof include a methyl group, and an ethyl group, a trifluoromethyl group, a n-propyl group, a n-butyl group, an isopropyl group, and a sec-butyl group. A methyl group, an ethyl group and a trifluoromethyl group are more preferable, and a methyl group and an ethyl group are still more preferable.

In formula (I), l represents an integer of from 3 to 6. In particular, l is more preferably an integer of from 3 to 5, still more preferably 4 or 5, furthermore preferably 5. The compound of formula (I) is more preferably a compound in which l is from 4 or 5 and $R^1$ is a methyl group, an ethyl group or a trifluoromethyl group, still more preferably a compound in which l is from 5 and $R^1$ is a methyl group or an ethyl group. Here, a compound in which l is 5 and $R^1$ is a methyl group is tolperisone. A compound in which l is 5 and $R^1$ is an ethyl group is eperisone. A compound in which l is 4 and $R^1$ is an ethyl group is inaperisone. A compound in which l is 4 and $R^1$ is a trifluoromethyl group is lanperisone.

The compound of formula (II) is known as a therapeutic drug for Alzheimer's dementia and cognitive disorder.

The action of the compound of formula (II) on fibrosis is not known at all. In particular, the compound of formula (II) has an effect of specifically inducing cell death on fibroblast cells, more preferably lung fibroblast cells. The compound of formula (II) has an effect of specifically suppressing activation of fibroblast cells, more preferably lung fibroblast cells. The compound of formula (II) has an effect of suppressing the fibrosing of tissues, particularly the fibrosing of lung tissues. The compound of formula (II) has an effect of suppressing a decrease in respiratory function. The compound of formula (II) has an effect of suppressing injury of tissues, particularly injury of lung tissues.

In formula (II), n is an integer of 8 to 12, more preferably 9 or 10, still more preferably 10. Here, the compound in which n is 10 is idebenone.

The salt of the compound of formula (I) or formula (II) is not particularly limited as long as it is a pharmaceutically acceptable salt, and examples thereof include mineral acid salts such as hydrochlorides, sulfates and nitrates, and organic acid salts such as acetates, oxalates, citrates and tartrates. Of these, hydrochlorides of the compound of formula (I) are more preferable.

Examples of the solvate of a compound of formula (I) or formula (II) or a pharmaceutically acceptable salt thereof include hydrates and alcoholates, and hydrates are more preferable.

The compound of formula (I) or formula (II) has been already known as described above, and can be produced in accordance with a known production method.

The compound of formula (I) or formula (II), or a pharmaceutically acceptable salt thereof or a solvate of the compound or the salt thereof has a selective cell death inducing action on lung fibroblast cells and an excellent pulmonary fibrosing suppressing action with an amount small enough not to injure alveolar epithelial cells, as shown in Examples below. Accordingly, such a compound is useful as a therapeutic drug for various fibroses. Here, examples of the fibrosis include pulmonary fibrosis, idiopathic pulmonary fibrosis, scleroderma, renal fibrosis, hepatic fibrosis, cardiac fibrosis, and fibroses in other organs or tissues. It is preferable to use the compound for pulmonary fibrosis and idiopathic pulmonary fibrosis, and it is particularly preferable to use the compound for idiopathic pulmonary fibrosis.

Therefore, the pharmaceutical composition containing a compound of formula (I) or formula (II), a pharmaceutically acceptable salt or a solvate of the compound or the salt thereof is useful as a composition for treating fibrosis, more preferably a composition for treating pulmonary fibrosis, still more preferably a composition for treating idiopathic pulmonary fibrosis.

Examples of the form of the pharmaceutical composition of the present invention include preparations for oral administration (e.g. tablets, coated tablets, powders, granules, capsules and liquids), preparations for airway administration, preparations for intraperitoneal administration, preparations for transvenous administration, injections, suppositories, patches and ointments, and preparations for oral administration, preparations for airway administration, and preparations for transvenous administration are preferable. Since a person skilled in the art recognizes that the administration route for intraperitoneal administration in animals is equivalent to the administration route for transvenous administration in humans, results of intraperitoneal administration in animals can be considered as results of transvenous administration in humans.

The above-mentioned dosage forms can be usually prepared by known methods using pharmaceutically acceptable carriers in addition to the foregoing active ingredients. Examples of such carriers include various carriers which are commonly used for usual drugs, for example excipients, binders, disintegrants, lubricants, diluents, solubilizing agents, suspending agents, tonicity agents, pH adjusters, buffers, stabilizers, colorants, flavoring agents and odor improvers.

While the dose of the pharmaceutical composition of the present invention varies in accordance with an administration route, sex, body weight, age, symptom and the like, typically the daily dose for adults is preferably from 0.5 mg to 3,000 mg, more preferably from 1 mg to 300 mg, in terms of the amount of the active ingredient. The daily dose may be given by single-dose administration or multiple-dose administration.

EXAMPLES

The present invention will be described in more detail by way of Examples.

Example 1 a. Experimental Method
(1) Administration of Bleomycin (BLM), Idebenone, Tolperisone and Eperisone On day 1, BLM was administered via the airway to a normally reared male ICR mouse to prepare a BLM pulmonary injury model mouse.

Pre-administration: Idebenone was administered via the airway once a day for a period from day 1 to day 7. On day 1, idebenone was administered via the airway one hour before administration of BLM.

Post-administration: Idebenone was administered via the airway once a day for a period from day 10 to day 18. Both the drugs were suspended in 0.9% NaCl and used.

Post-administration: Tolperisone was administered via the airway once a day for a period from day 10 to day 19. Both the drugs were suspended in 0.9% NaCl and used.

Post-administration: Eperisone was administered via the airway once a day for a period from day 10 to day 19. Both the drugs were suspended in 0.9% NaCl and used.

Since a person skilled in the art recognizes that the administration route for intraperitoneal administration in animals is equivalent to the administration route for transvenous administration in humans, results of intraperitoneal administration in animals can be considered as results of transvenous administration in humans.
(2) Real-Time RT-PCR Total RNA of cells was extracted by using RNeasy kit (Qiagen). 2.5 μg of total RNA was subjected to reverse transcription reaction in accordance with the protocol from Takara Bio Inc by using a first-strand cDNA synthesis kit (Takara Bio Inc). The synthesized cDNA was analyzed with a CFX96 (trademark) real time system by using SsoFast EvaGreen Supermix. For equalizing the total RNA amounts in the reactions, a glyceraldehyde-3-phosphate dehydrogenase (GAPDH) gene was used as an internal standard.
(3) Cell Culture A549 cells (human alveolar epithelial cells) and LL29 cells (IPF patient-derived lung fibroblast cells) were cultured under conditions of 37° C. and 5% $CO_2$ by using, respectively, Dulbecco's modified Eagle's medium containing 10% FBS and Ham's F-12K (Kaighn's) medium containing 15% FBS.

The number of living cells was measured by an MTT method or trypan blue staining using Countess (trademark) Automated Cell Counter (Invitrogen, Carlsbad, CA). For evaluation of cell death, LDH activity in the medium was measured in accordance with the protocol of the assay kit.

(4) Histological Staining Method and Immunohistological Staining Method

Isolated lung tissues were fixed with 10% formalin for 24 hours, and then embedded in paraffin to prepare a paraffin section with a thickness of 4 μm.

H&E staining was performed in the following manner: the section was stained with Mayer's hematoxyline, and then stained with a 1% eosin solution. After the staining, the section was encapsulated with malinol, and histologically analyzed by using a Nanozoomer-XR digital slide scanner (Hamamatsu Photonics, Shizuoka, Japan) or Olympus BX51 Microscope (Tokyo, Japan).

Masson's trichrome staining was performed by using a first staining solution (5 w/v % potassium dichromate and 5 w/v % trichloroacetic acid), Weigert's iron hematoxylin, a second staining solution (1.25 w/v % phoaphotangstenicacid and 1.25 w/v % phosphomolybdic acid), a 0.75 w/v % orenge G, a xylidine ponceau mixed solution (0.12 w/v %, xylidine ponceau, 0.04 w/v % acid fchsin and 0.02 w/v % azophloxin) and aniline blue. After the staining, the section was encapsulated with malinol, and histologically analyzed by using a Nanozoomer-XR digital slide scanner. Pulmonary fibrosing was ranked by Ashcroft scores. For the Ashcroft score, J. Clin. Pathol. 41, 467-470 (1988) was used as a reference.

A method for immunostaining with α-SMA was carried out by blocking the section with 2.5% goat serum for 10 minutes, and then performing a primary antibody treatment (against α-SMA, 1:100 dilution). At 12 hours later, the section was incubated with Alexa Fluor 594 goat anti-rabbit immunoglobulin G and DAPI for 2 hours. Thereafter, the section was encapsulated by using VECTA SHIELD. The section was photographed by using a microscope (Olympus DP71).

An α-SMA-positive region was quantitatively determined by using Image J software (National Institutes of Health, Bethesda, MD) The number of 8-OHdG-positive cells was quantitatively determined by using Definiens Tissue Studio (trademark) software (CTC Life Science Corporation, Tokyo, Japan).
(5) Measurement of Lung Function and Forced Vital Capacity The lung function was measured in accordance with previous literature by using a computer-controlled ventilator for small animals (FlexiVent; SCIREQ, Montreal, Canada). A metal tube (with an outer diameter of 1.27 mm and an inner diameter of 0.84 mm) was inserted by 8 mm into a mouse anesthetized with chloral hydrate (500 mg/kg), and the mouse was caused to breathe mechanically at a rate of 150 breaths/min with a tidal volume of 8.7 ml/kg and a positive end-expiratory pressure ventilation of 2-3 cm $H_2O$.

The total respiratory elastance and the tissue elastance were measured by the snap shot and the forced oscillation technique, respectively. The forced vital capacity was measured in accordance with Chest 142, 1011-1019 (2012) by using the computer-controlled ventilator for small animals and a negative pressure reservoir (SCIREQ, Montreal, Canada). All the data was analyzed by using FlexiVent software (version 5.3; SCIREQ, Montreal, Canada).
(6) Quantitative Determination of Hydroxyproline The isolated left upper lobe of the lung of the mouse was homogenized in 0.5 mL of 5% TCA, and the mixture was centrifuged to obtain a precipitate. 0.5 mL of concentrated hydrochloric acid was added to the precipitate, and the mixture was heated at 110° C. for 16 hours. Thereby, the precipitate was hydrolyzed, to extract hydroxyproline. 1.4 w/v % chloramine T was added to the extracted hydroxyproline, and the mixture was left to stand for 20 minutes, and then heated at 65° C. for 10 minutes together with an Ehrich's reagent (1 M DMBA, 70 v/v % isopropanol and 30 v/v % perchloric acid) to give a red or violet color. Thereafter, the absorbance (550 nm) was measured.

(7) Statistical Analysis

All values are shown in terms of a mean±standard error (standard error of the mean; SEM). The significance test was conducted by One-way ANOVA. The Dunnett's test was applied to the comparison among multiple groups, and the Student's t-test was applied to the comparison between two groups. For the test, SPSS22 software was used. It was determined that there was a significant difference when the P value was less than 0.05.

*: $p<0.05$ (versus vehicle), ** $p<0.01$ (versus vehicle), #: $p<0.05$ (versus BLM alone), ##: $p<0.01$ (versus BLM alone)

b-1. Results (1) Effect of Idebenone on Cell Death and Cell Proliferation

It is considered that activation of lung fibroblast cells is important in the IPF fibrosing mechanism. It has been heretofore reported that in the IPF patient's lung, fibroblast cells are unusually proliferated and activated, and collagen is unusually produced from the activated lung fibroblast cells. Thus, the present inventors carried out a screening test among existing approved drugs to identify drugs which selectively act on lung fibroblast cells without injuring alveolar epithelial cells. In the screening test, a decrease in cell viability of lung fibroblast cells by the compound was used as a simplified index for suppression of activity of lung fibroblast cells.

For a specific method, IPF patient-derived lung fibroblast cells (LL29 cells) and human alveolar epithelial cells (A549 cells) were treated with existing approved drugs, and the cell viability 24 hours later was evaluated by an MTT method. As a result, idebenone, a compound for which there was a particularly marked difference in value of $IC_{50}$ (concentration required to decrease the cell viability by 50%) for between LL29 and A549 cells, was selected from compounds of which the value of $IC_{50}$ for LL29 cells was lower than that for A549 cells.

Figure 1B:
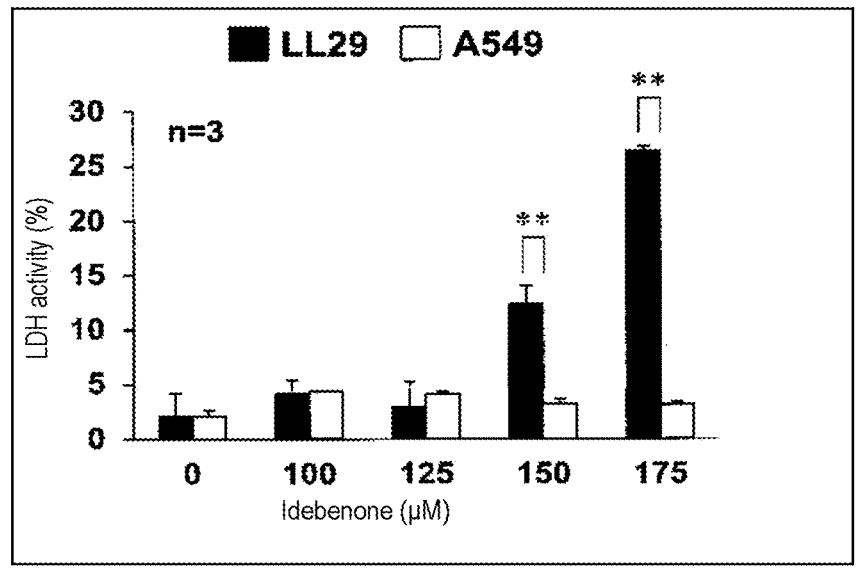
FIG. 1B shows an action of idebenone on LDH activity of LL29 cells and A549 cells.

More minute doses than the doses used during screening test were applied to examine the cell death inducing action of idebenone and to simultaneously conduct a screening reproducibility experiment. The results showed that idebenone decreased the cell viability of LL29 cells (lung fibroblast cells) at a concentration lower than a concentration at which the cell viability of A549 cells (alveolar epithelial cells) decreased (FIG. 1A). Next, LDH released from the cells was quantitatively determined to evaluate cell death, and the results showed that LDH was released into the medium with idebenone (150 µM) for LL29 cells, whereas little LDH was released for A549 cells (FIG. 1B). From the results, it was shown that idebenone selectively induced cell death more on LL29 cells than on A549 cells.

Figure 1C:
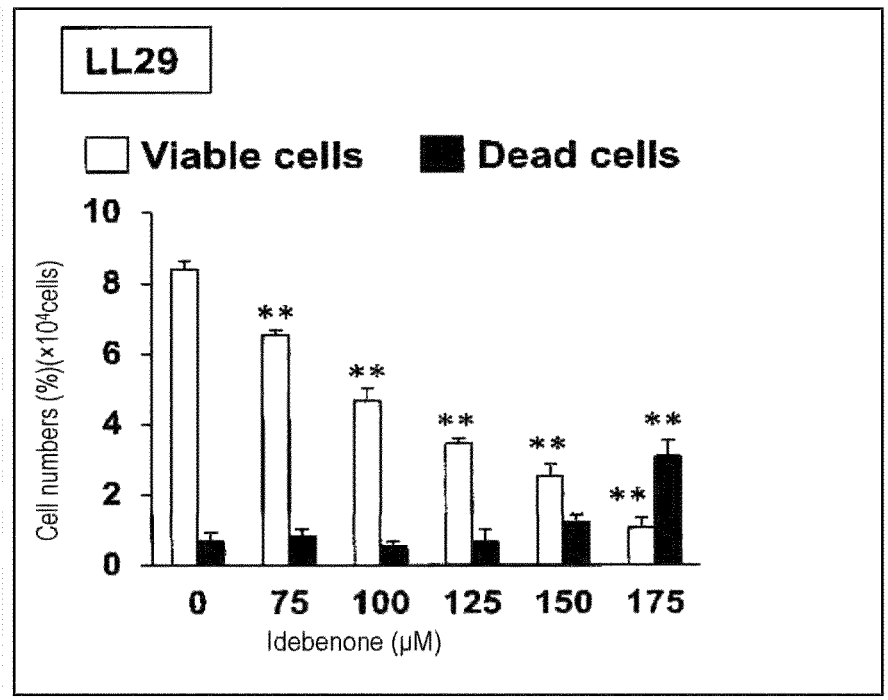
FIG. 1C shows an action of idebenone on cell death of LL29 cells.
Figure 1D:
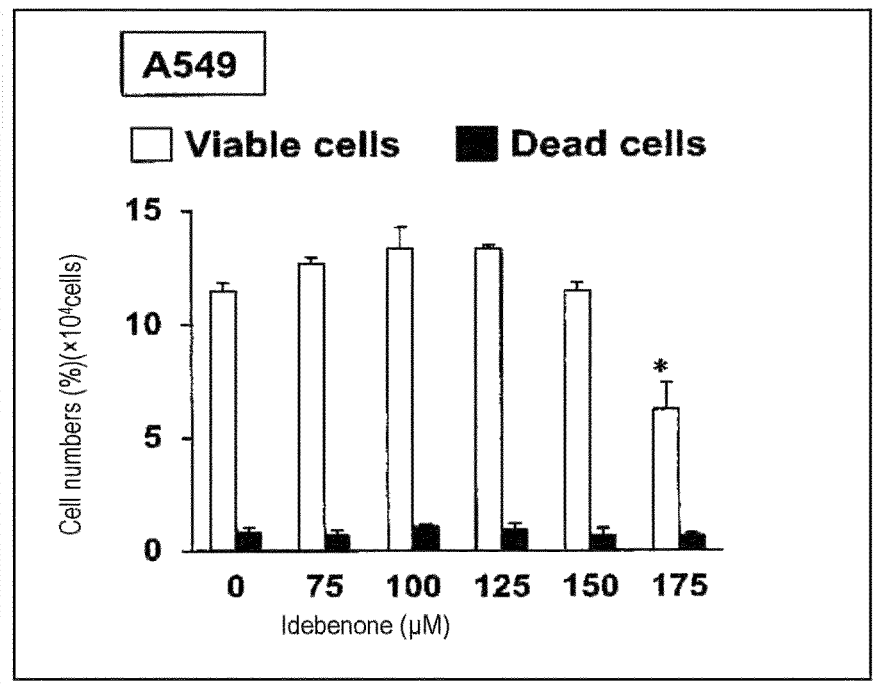
FIG. 1D shows an action of idebenone on cell death of A549 cells.

As is apparent from FIGS. 1A and 1B, there was the possibility that idebenone suppressed cell proliferation of LL29 cells at 75 to 125 µM. Thus, the present inventors measured the number of living cells and the number of dead cells with the aid of trypan blue staining. The results showed that idebenone started to suppress proliferation of LL29 cells at 75 µM, and started to induce cell death of LL29 cells at 175 µM (FIG. 1C). On the other hand, in the epithelial cells, idebenone started to suppress cell proliferation at 175 µM, and did not induce cell death at examined concentrations (FIG. 1D).

Figure 2:
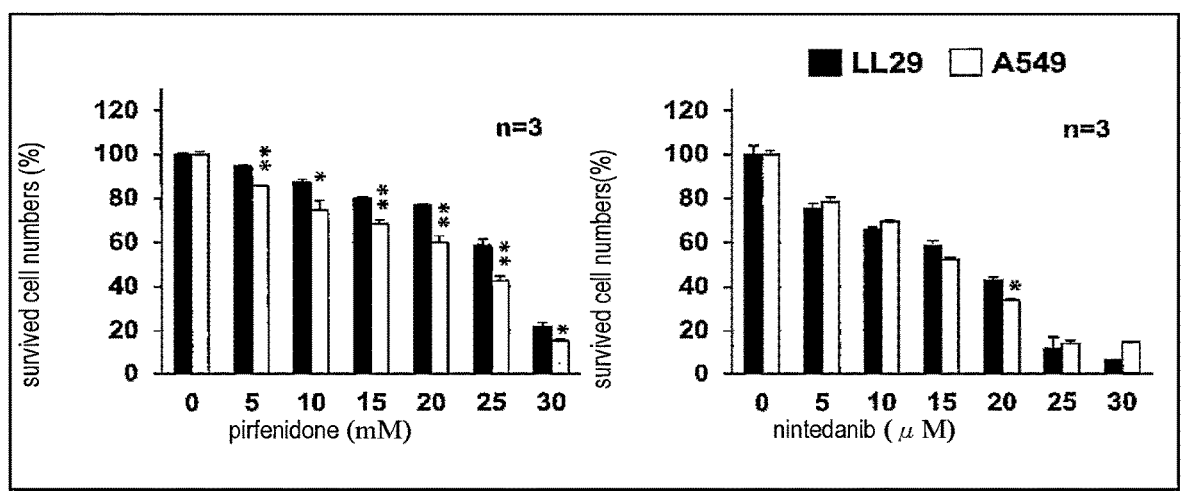
FIG. 2 shows actions of pirfenidone and nintedanib on survived cell number (%) of LL29 cells and A549 cells.

In addition, cell death was examined with pirfenidone and nintedanib which are existing therapeutic drugs for IPF, and the results showed that these two drugs did not induce fibroblast cell-selective cell death (FIG. 2).

(2) Effect of Idebenone on Bleomycin (BLM)-Dependent Pulmonary Fibrosing

With regard to development of idebenone as a therapeutic drug for IPF, it is important to exhibit an effect in IPF animal models as well. As IPF animal models, bleomycin (BLM) pulmonary injury models are often used. BLM pulmonary injury models have been reported to reproduce typical characteristics of pathological conditions of IPF, and it has been heretofore reported that airway administration of BLM injures alveolar epithelial cells, proliferates and accumulates lung fibroblast cells, and decreases the respiratory function. Thus, the prophylactic and therapeutic effects of idebenone on pulmonary fibrosing were examined by using BLM pulmonary injury models.

Figure 3A:
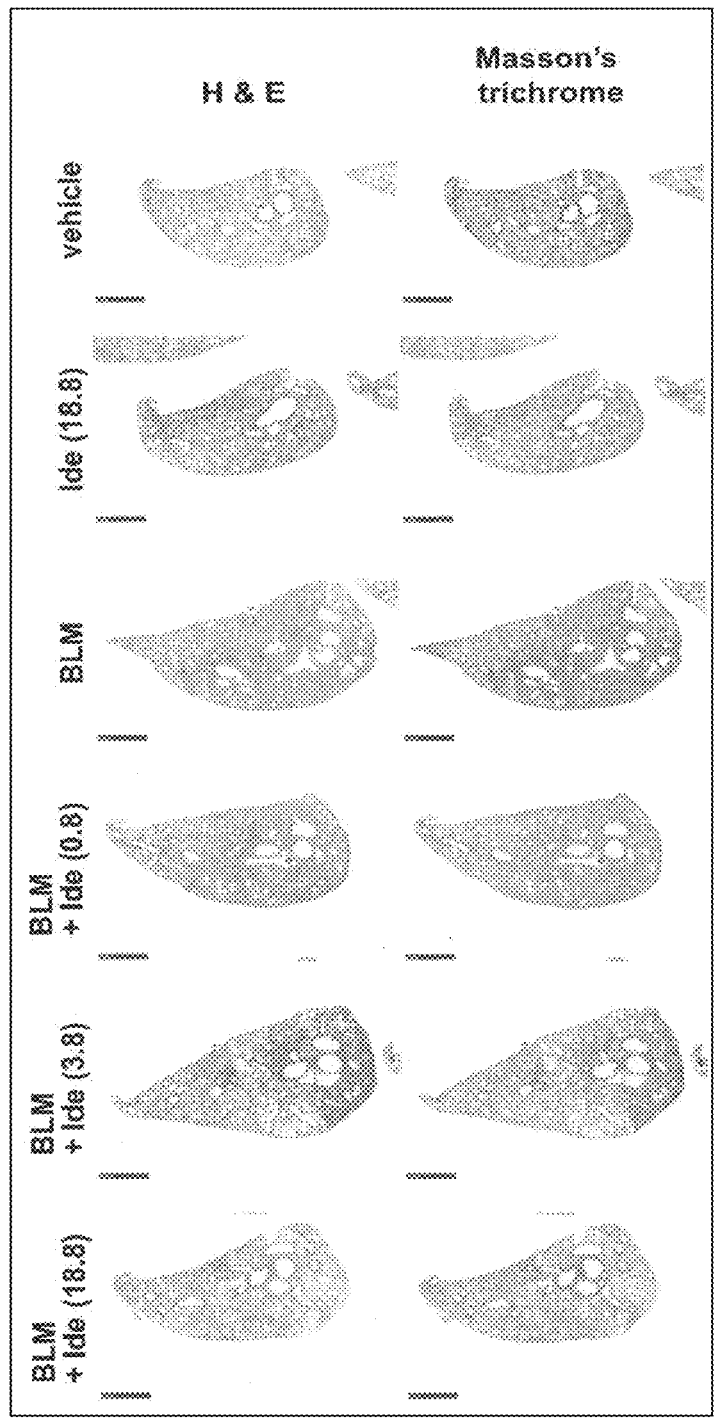
FIG. 3A shows an action of idebenone (ide) on BLM-dependent pulmonary fibrosing (collagen staining).
Figure 3B:
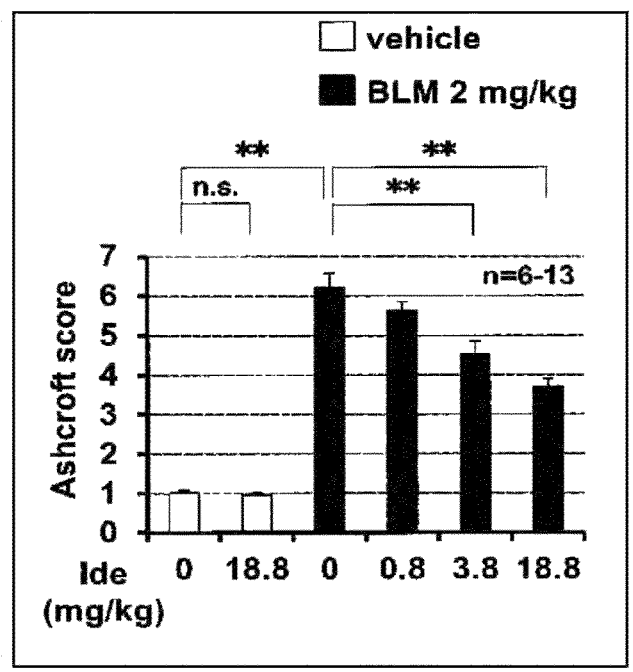
FIG. 3B shows an action of idebenone (Ide) on BLM-dependent pulmonary fibrosing (Ashcroft scores).
Figure 3C:
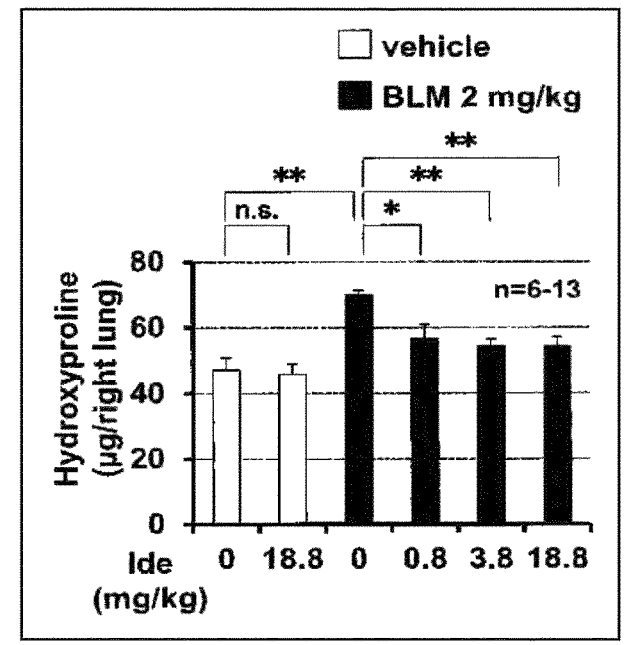
FIG. 3C shows an action of idebeone on BLM-dependent pulmonary fibrosing (hydroxyproline amount).

BLM was administered via the airway to a mouse, and collagen was stained by H&E staining and Masson's trichrome staining, and it was confirmed that pulmonary injuries (thickening, and edemas of alveolar walls and stroma) and collagen accumulation occurred in a BLM-dependent manner. Airway administration of idebenone markedly suppressed such injuries and collagen accumulation (FIG. 3A). Further, the effect of idebenone on BLM-dependent pulmonary fibrosing was evaluated by using as indices the Ashcroft score of fibrosing quantitatively determined on the basis of a tissue image and the amount of hydroxyproline which is an amino acid contained abundantly in collagen of the lung. The Ashcroft score and the amount of hydroxyproline increased in a BLM-dependent manner, and administration of idebenone markedly suppressed such an increase (FIGS. 3B and 3C).

Figure 3D:
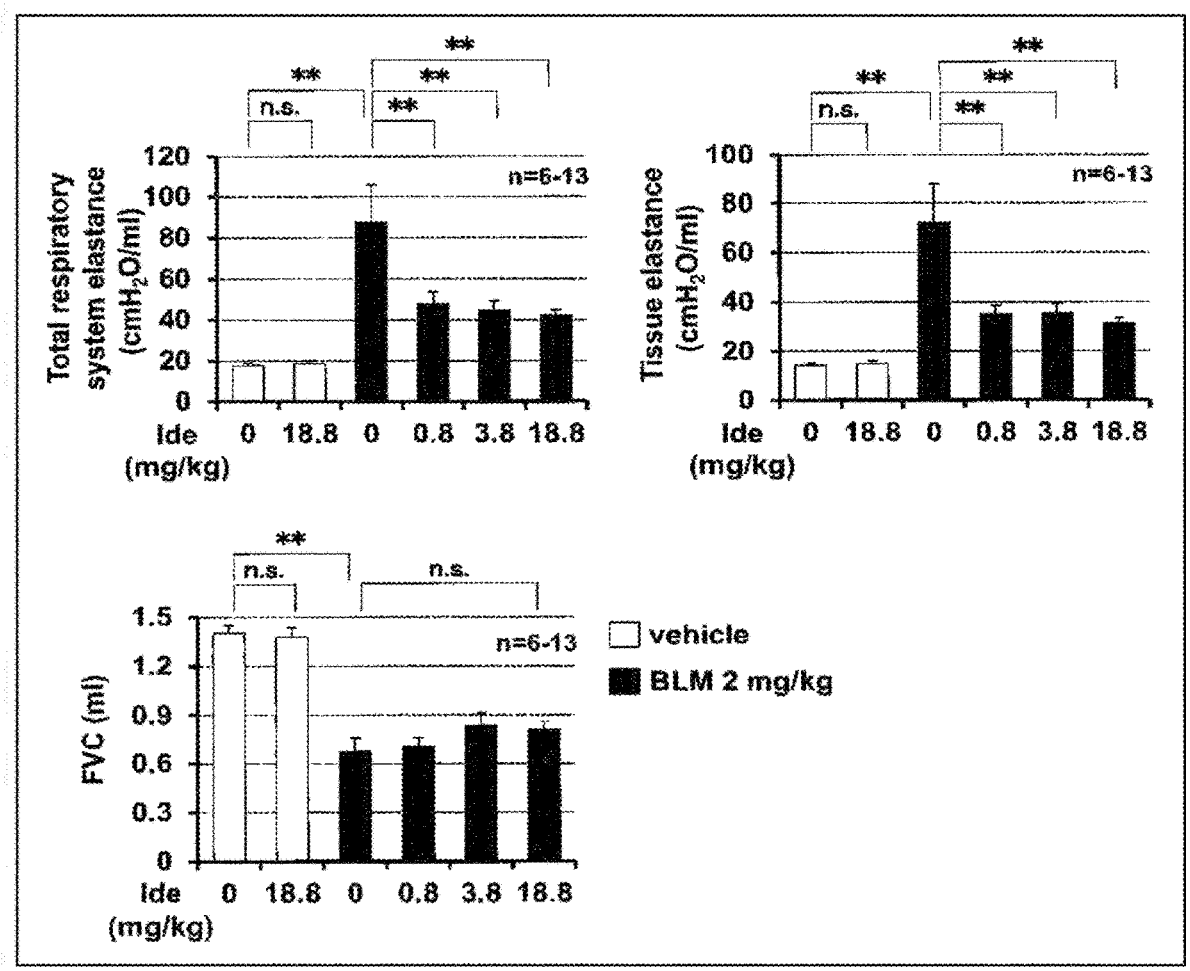
FIG. 3D shows an action of idebenone (Ide) on BLM-dependent pulmonary fibrosing (total lung and bronchi elastance, FVC).

From the viewpoint of clinical application of idebenone, it is important to exhibit an effect in not only histological indices but also indices such as a respiratory function. It has been heretofore reported that in IPF patients, the lung becomes hardened due to fibrosing, so that the lung elastance increases, leading to a decrease in forced vital capacity (FVC). Thus, the present inventors measured these indices by using a ventilator for mice. Administration of BLM increased the total respiratory system elastance (elastance of the total lung including bronchi, small bronchi and alveolus) and the tissue elastance (alveolar elastance), and airway administration of idebenone suppressed such an increase (FIG. 3D). FVC decreased in a BLM-dependent manner, and airway administration of idebenone tended to suppress such a decrease (FIG. 3D). The above results showed that airway administration of idebenone suppressed BLM-dependent pulmonary fibrosing and a BLM-dependent decrease in respiratory function. Airway administration of idebenone (18.8 mg/kg) alone did not affect pulmonary fibrosing and the respiratory function (FIGS. 3A to 3D).

(3) Therapeutic Effect of Idebenone on BLM-Dependent Pulmonary Fibrosing

Figure 4A:
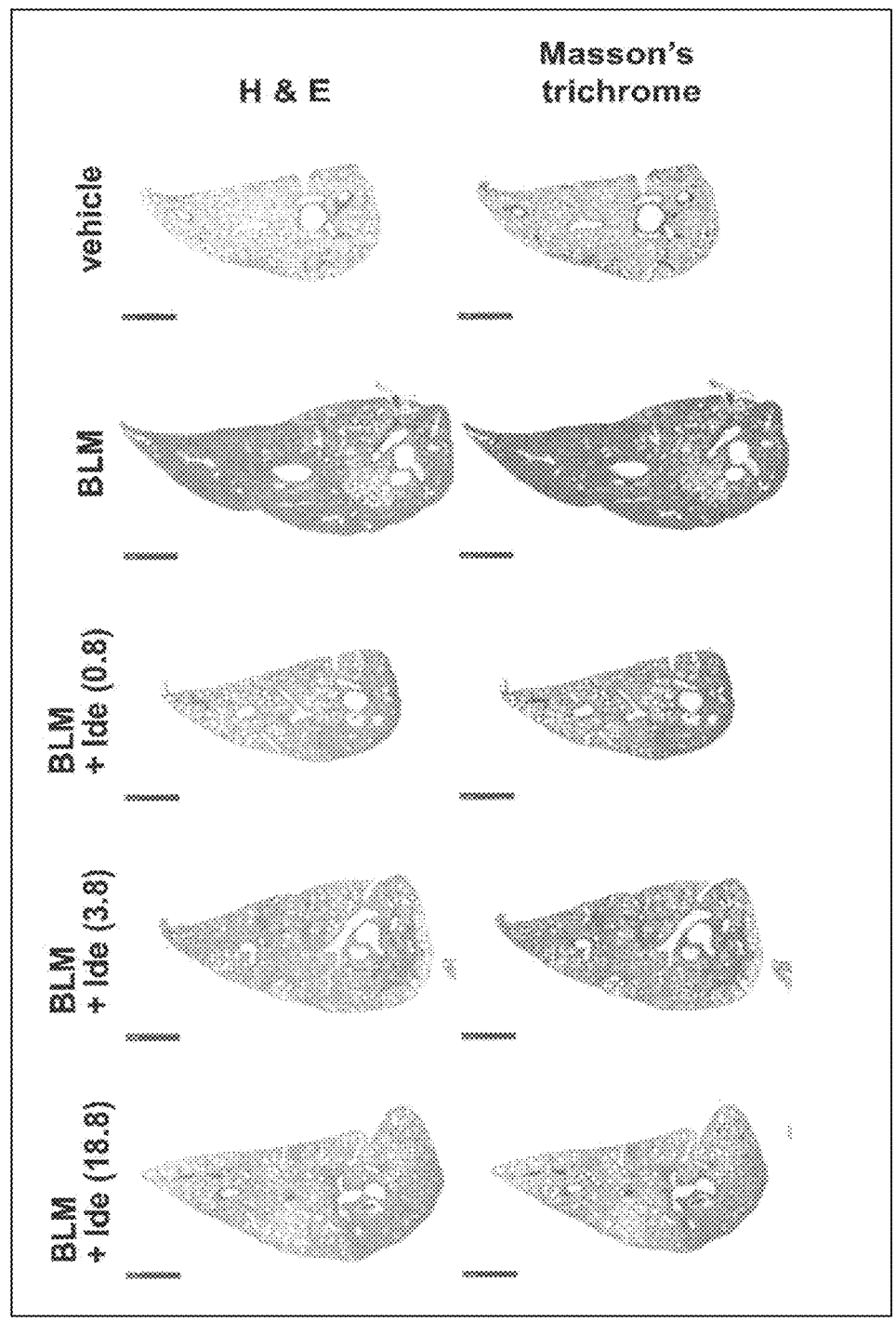
FIG. 4A shows a therapeutic effect of idebenone (Ide) on BLM-dependent pulmonary fibrosing (collagen staining).
Figure 4B:
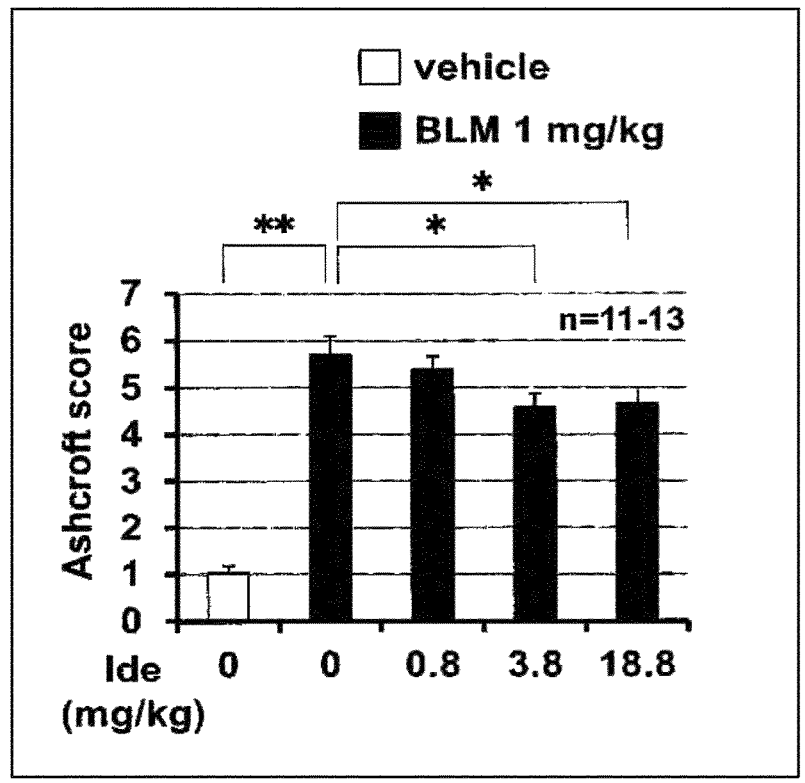
FIG. 4B shows a therapeutic effect of idebenone (Ide) on BLM-dependent pulmonary fibrosing (Ashcroft scores).
Figure 4C:
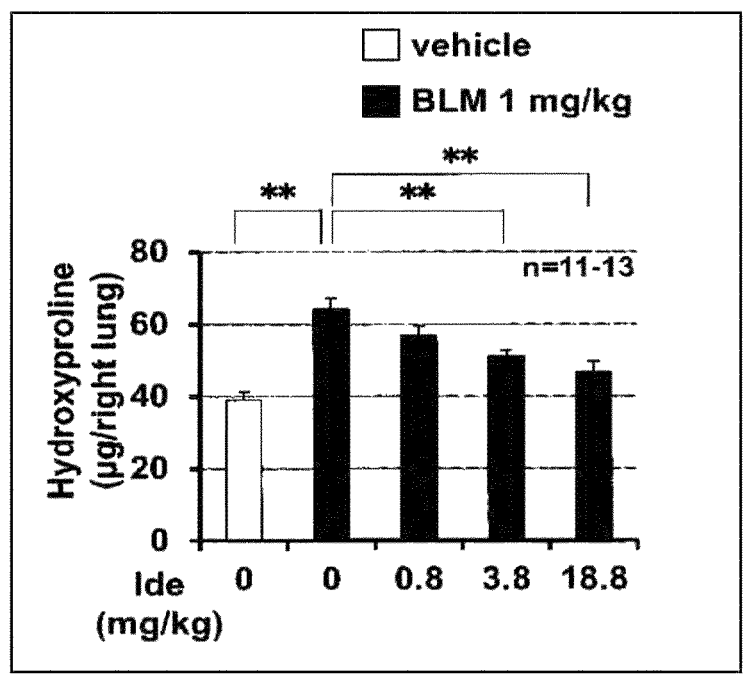
FIG. 4C shows a therapeutic effect of idebenone on BLM-Dependent pulmonary fibrosing (hydroxyproline amount).
Figure 4D:
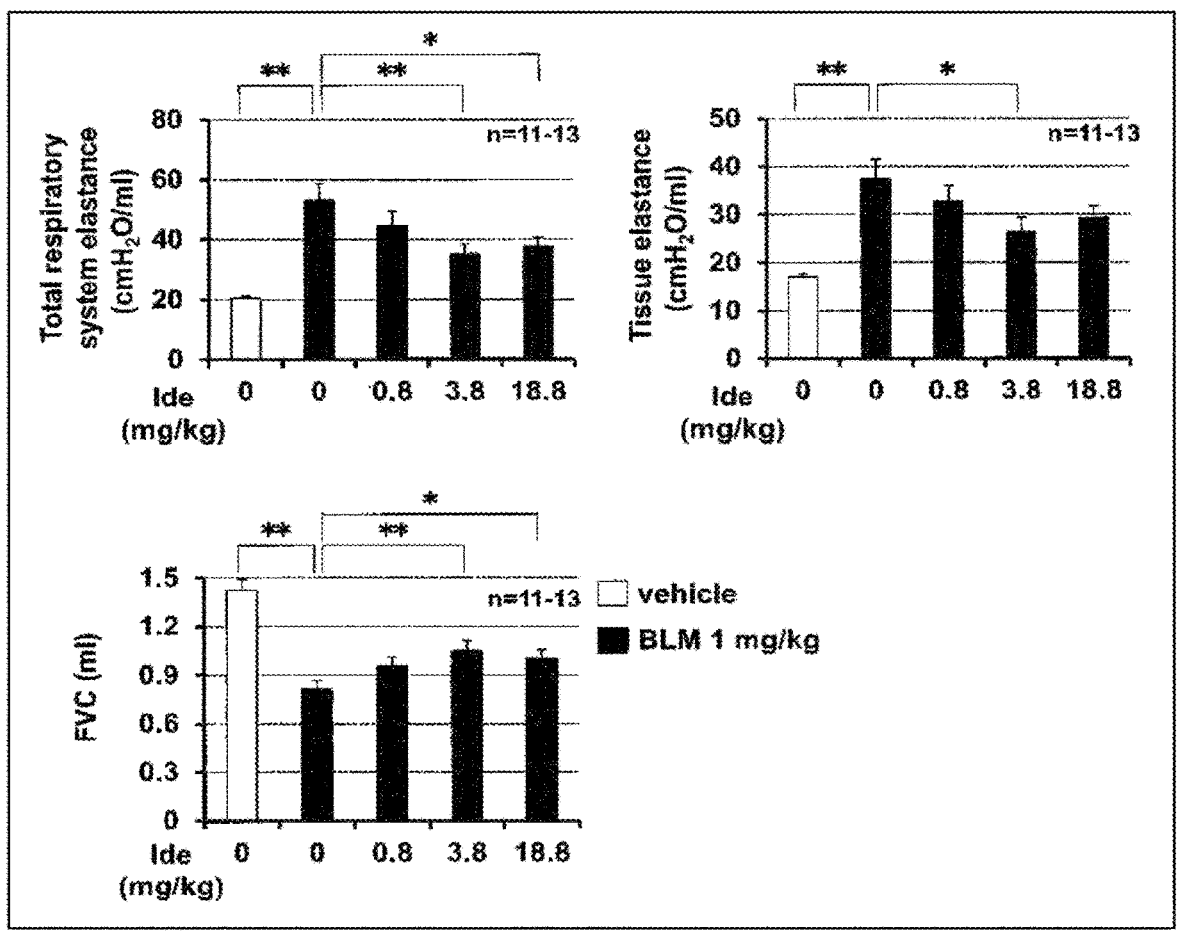
FIG. 4D shows a therapeutic effect of idebenone on BLM-dependent pulmonary fibrosing (total lung and bronchi elastance, FVC).

Next, the present inventors examined the therapeutic effect by administering idebenone to a mouse in which fibrosing had been induced by administration of BLM in advance. It has been heretofore reported that about 10 days after administration of BLM, pulmonary fibrosing occurs. Thus, the present inventors started airway administration of idebenone 10 days after administration of BLM, and evaluated the pulmonary fibrosing and the respiratory function 20 days after administration of BLM. Airway administration of idebenone markedly suppressed pulmonary injury and fibrosing 20 days after administration of BLM (FIGS. 4A to 4C). Further, airway administration of idebenone markedly suppressed a BLM-dependent decrease in respiratory function (FIG. 4D). The above results showed that idebenone improved BLM-dependent pulmonary fibrosing and a BLM-dependent decrease in respiratory function even in a mouse in which fibrosing had been induced by administration of BLM in advance.

(4) Comparison of Idebenone with CoQ10

Figure 5A:
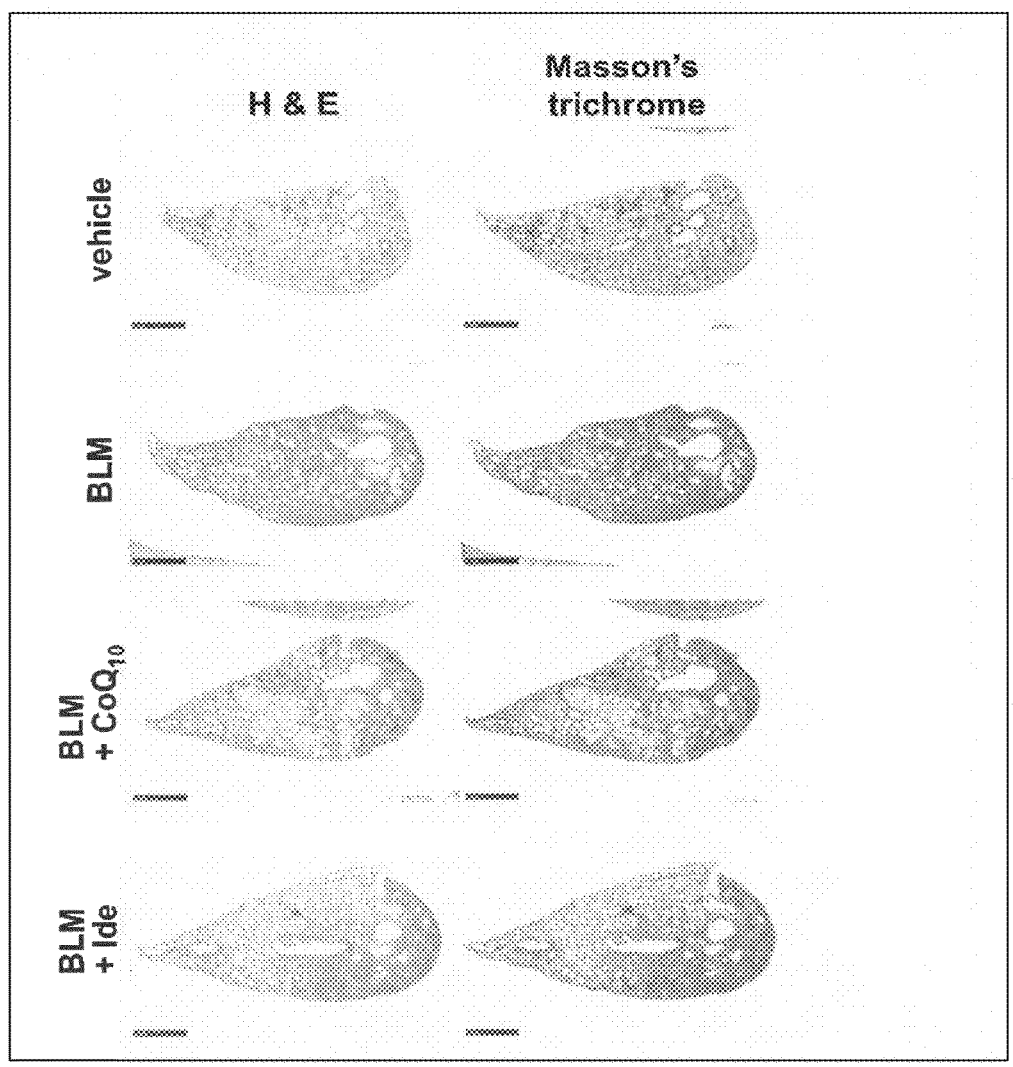
FIG. 5A shows actions of idebenone (Ibe) and CoQ10 on BLM-dependent pulmonary fibrosing (collagen staining).
Figure 5B:
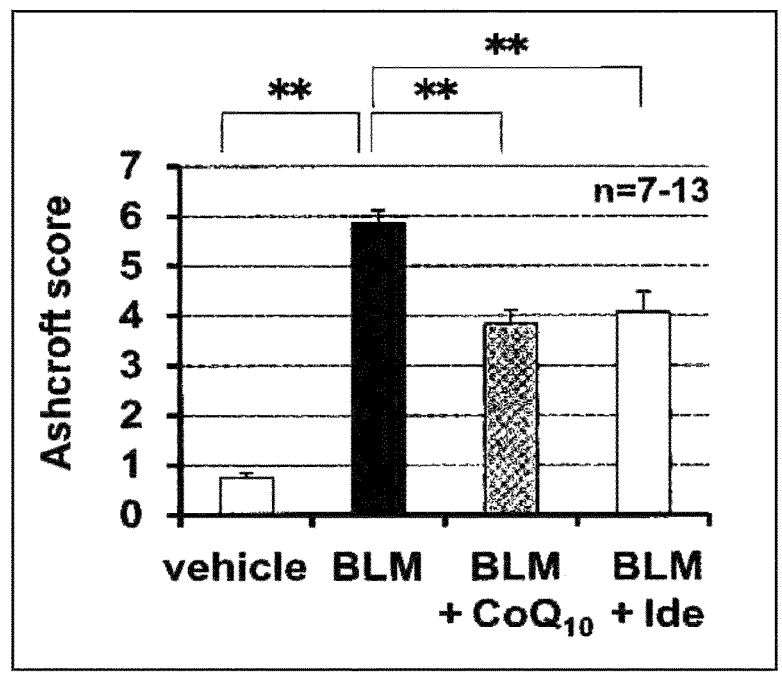
FIG. 5B shows actions of idebenone (Ide) and CoQ10 on BLM-dependent pulmonary fibrosing (Ashcroft scores).
Figure 5C:
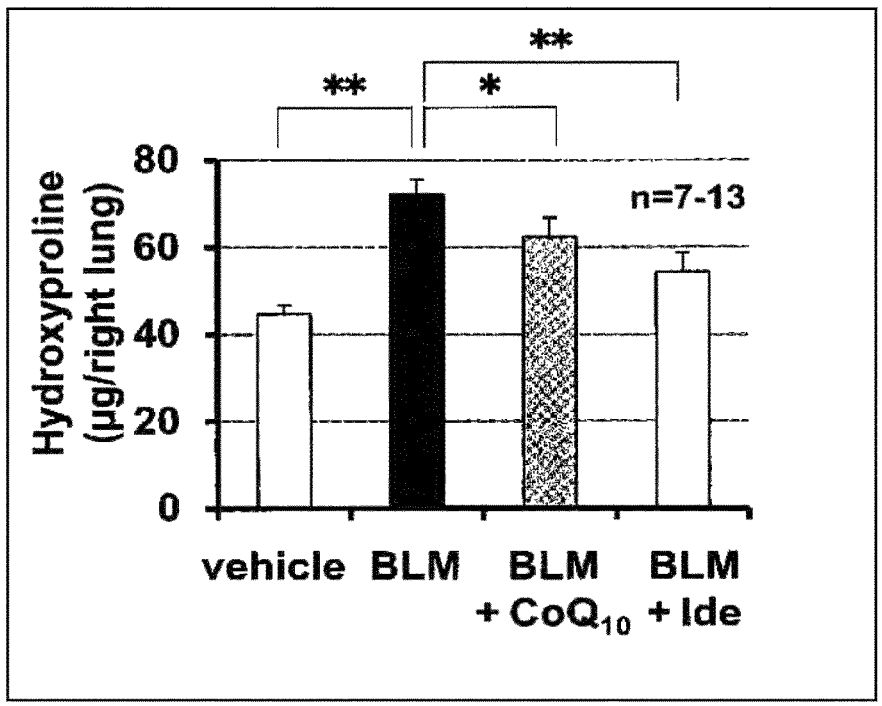
FIG. 5C shows actions of idebenone (Ide) and CoQ10 on BLM-dependent pulmonary fibrosing (hydroxyproline amount).

In order to understand a mechanism for determining the effect on idebenone, the present inventors compared the effects of idebenone and COQ10 on bleomycin pulmonary fibrosis. As shown in FIGS. 5A to 5C, pulmonary injury and fibrosing by bleomycin were suppressed by airway administration of idebenone or CoQ10.

Figure 6A:
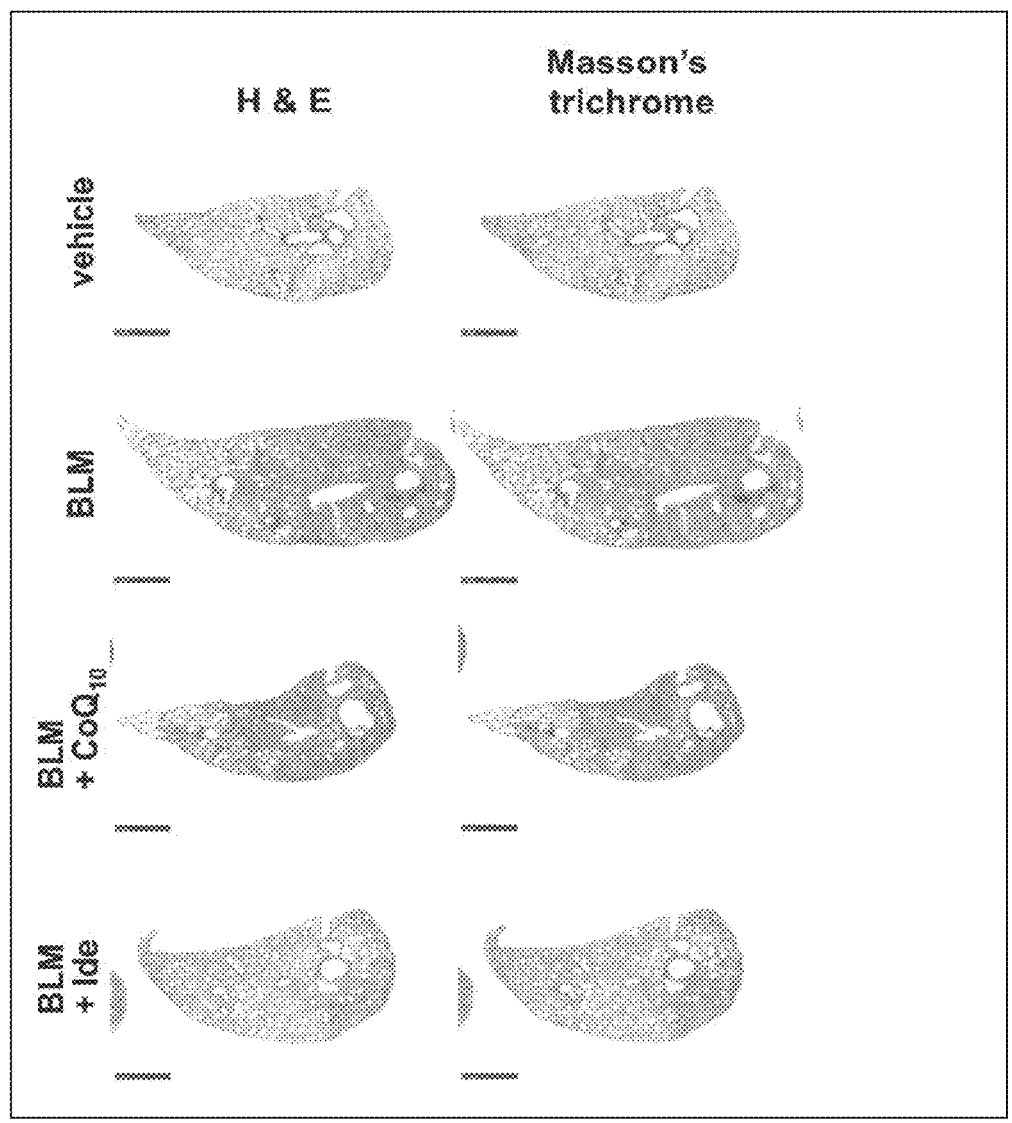
FIG. 6A shows actions of idebenone (Ide) and CoQ10 on BLM-Dependent pulmonary fibrosing (collagen staining).
Figure 6B:
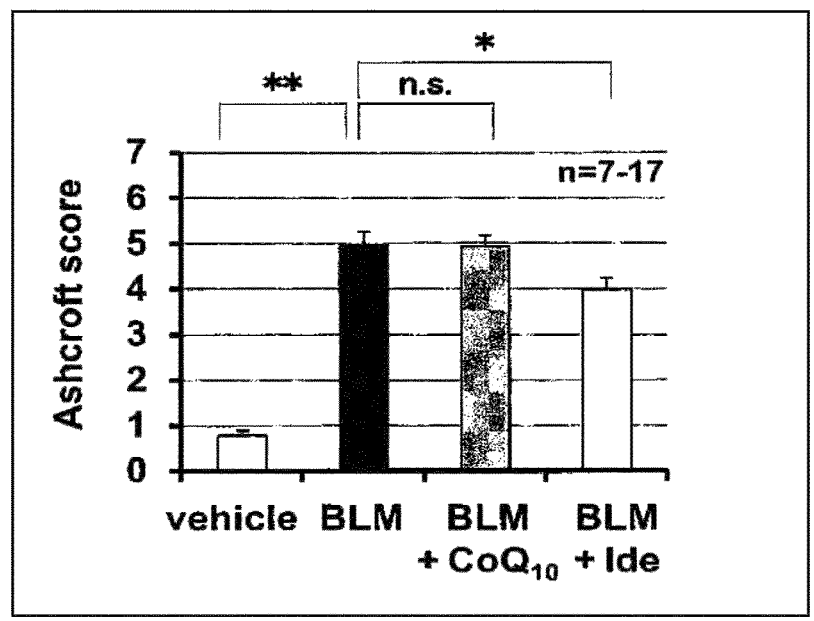
FIG. 6B shows actions of idebenone (Ide) and CoQ10 on BLM-dependent pulmonary fibrosing (Ashcroft scores).
Figure 6C:
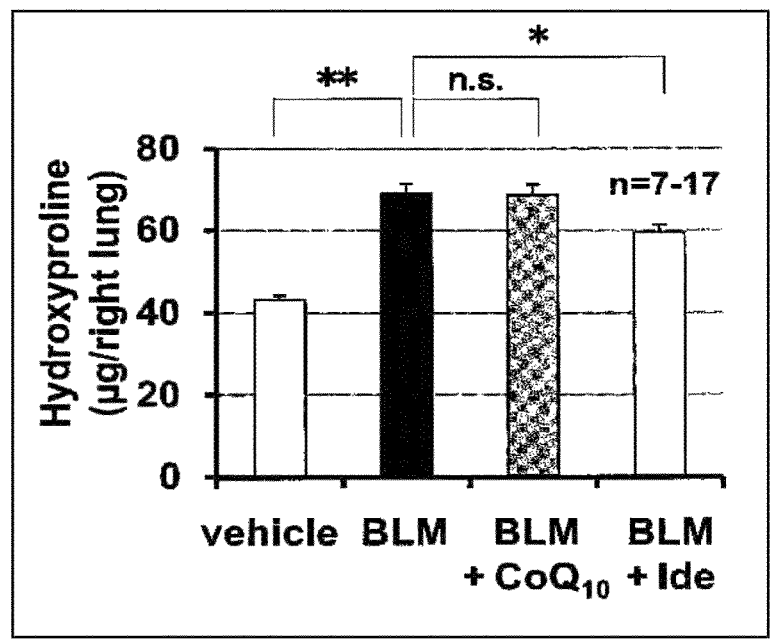
FIG. 6C shows actions of idebenone (Ide) and CoQ10 on BLM-dependent pulmonary fibrosing (hydroxyproline amount).

Next, the therapeutic effects of idebenone and CoQ10 on BLM pulmonary fibrosing were compared. As shown in FIGS. 6A to 6C, pulmonary injury and fibrosing by bleomycin were suppressed by idebenone, but were not suppressed by CoQ10.

Figure 7A:
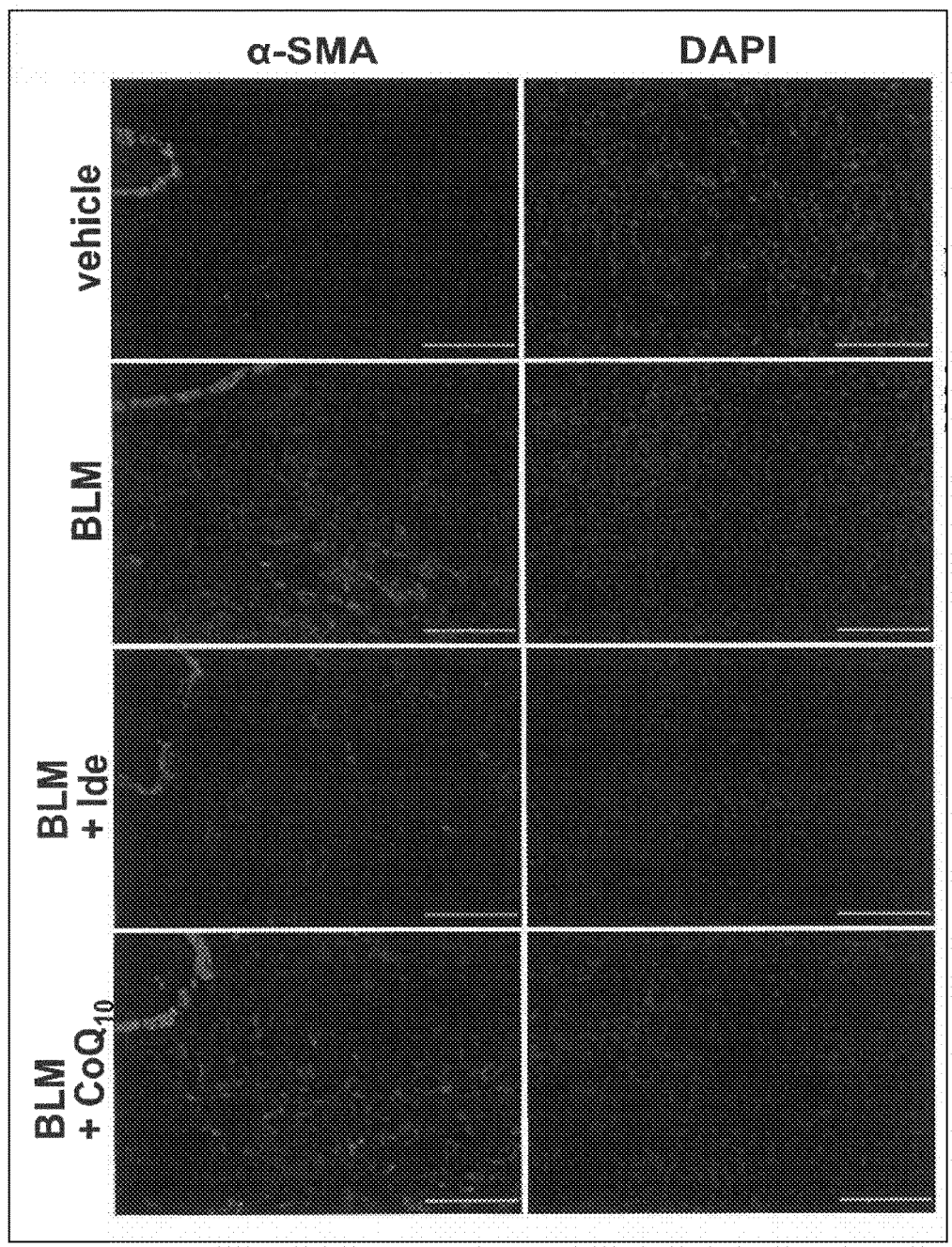
FIG. 7A shows effects of idebenone (Ide) and CoQ10 on myofibloblast cells (α-SMA cell stained).
Figure 7B:
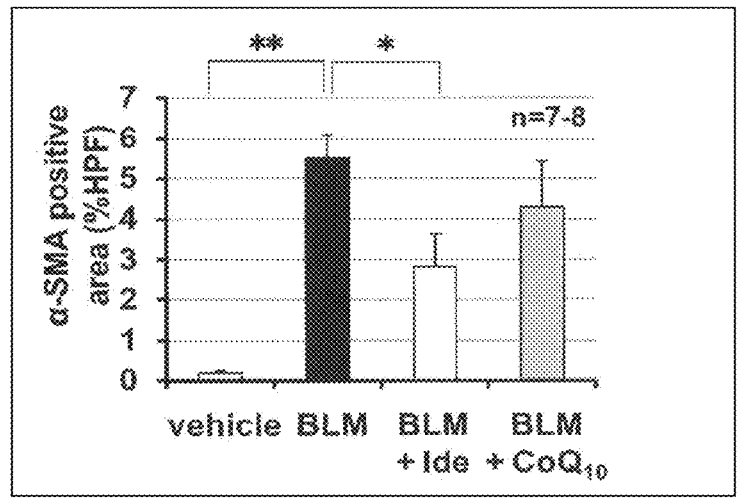
FIG. 7B shows idebenone (Ide) and CoQ10 on myofibloblast cells (number of α-SMA positive cells).
Figure 8A:
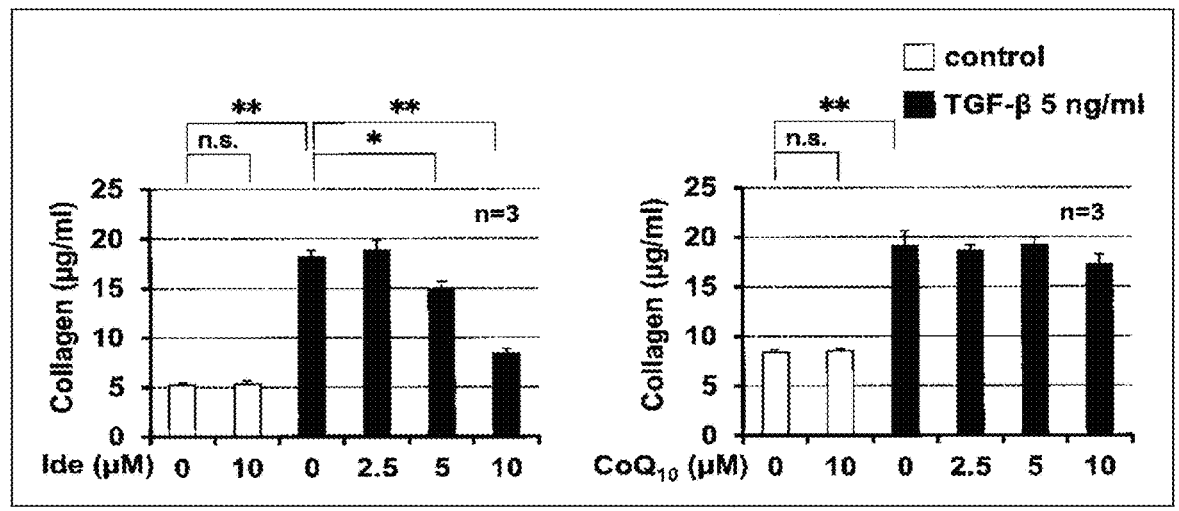
FIG. 8A shows actions of idebenone (Ide) and CoQ10 on collagen.
Figure 8B:
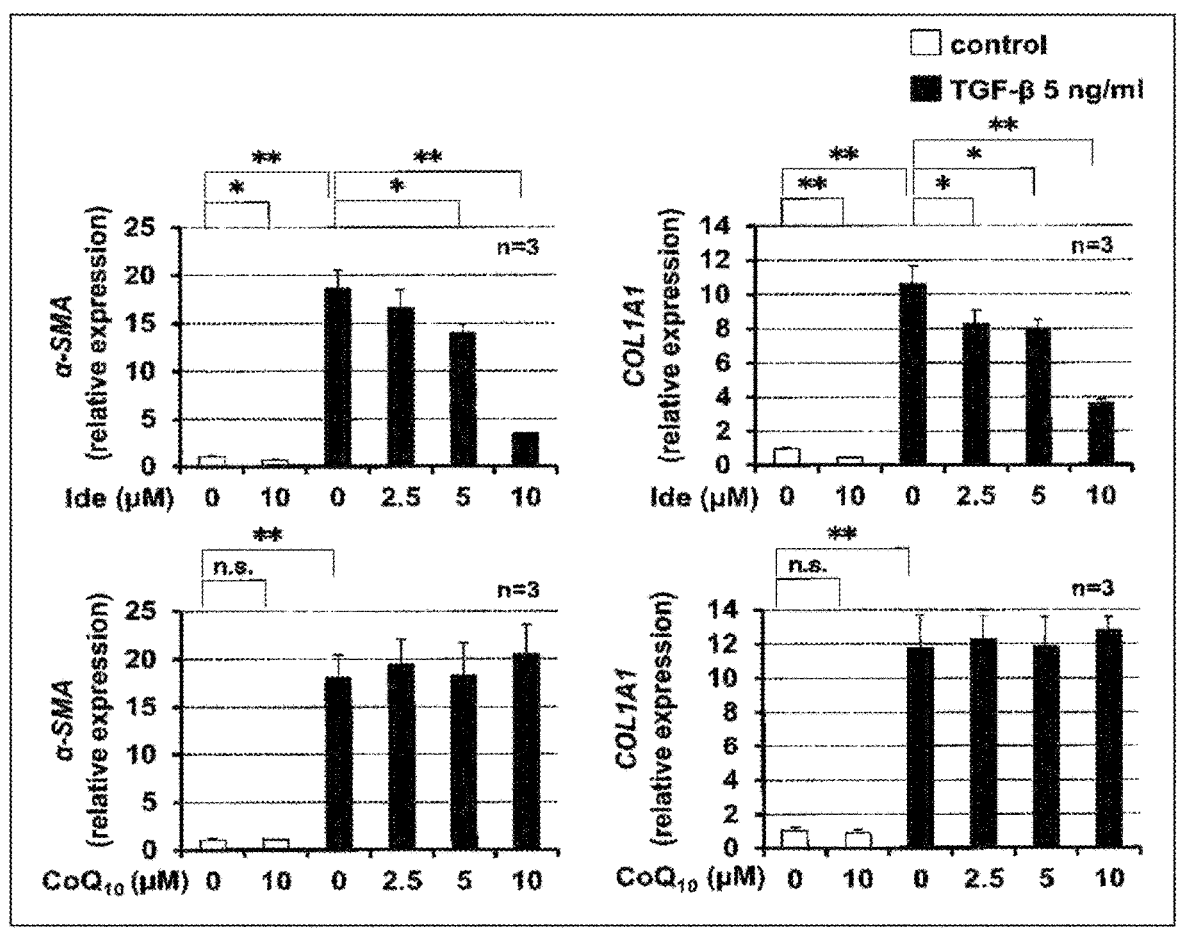
FIG. 8B shows actions of idebenone (Ide) and CoQ10 on α-SMA and COL1A1.

As described above, myofibroblast cells played an important role on pulmonary fibrosis in patients with IPF and bleomycin-induced pulmonary fibrosis. Thus, with attention focused on myofibroblast cells, the effects of idebenone and COQ10 were examined. As shown in FIGS. 7A and 7B, administration of bleomycin increased the number of α-SMA-positive cells (myofibroblast cells) of the lung, and idebenone markedly suppressed such an increase. In contrast, CoQ10 did not exhibit such a suppressing effect. Thus, the effects of idebenone and CoQ10 on TGF-β1-dependent activation of lung fibroblast cells (differentiation into myofibroblast cells) were compared. LL29 cells were treated with idebenone or CoQ10, and then treated with TGF-β1, and the amount of collagen in the medium was measured. As shown in FIG. 8A, the treatment with TGF-β1 increased the amount of collagen, and idebenone suppressed such an increase. In contrast, CoQ10 did not suppress such an increase. Next, the effect of idebenone was examined by using the levels of α-SMA and mRNA of collagen as indices. As shown in FIG. 8B, treatment of LL29 cells with TGF-β1 induced expression of α-SMA and Col1a1 mRNA, and treatment of LL29 cells with idebenone suppressed such induction. In contrast, CoQ10 did not suppress such induction. These results show that idebenone acted on fibroblast cells to suppress activation of lung fibroblast cells.

b-2. Results (1) Effect of Tolperisone on Cell Death

As with (b-1) above, IPF patient-derived lung fibroblast cells (LL29 cells) and human alveolar epithelial cells (A549 cells) were treated with existing approved drugs, and the cell viability 24 hours later was evaluated by an MTT method. As a result, among the compounds whose $IC_{50}$ values for LL29 cells were lower than those for A549 cells, tolperisone was selected, a compound exhibiting a particularly marked difference in $IC_{50}$ value (concentration required to decrease the cell viability by 50%) for between both LL29 and A549 cells.

Figure 9A:
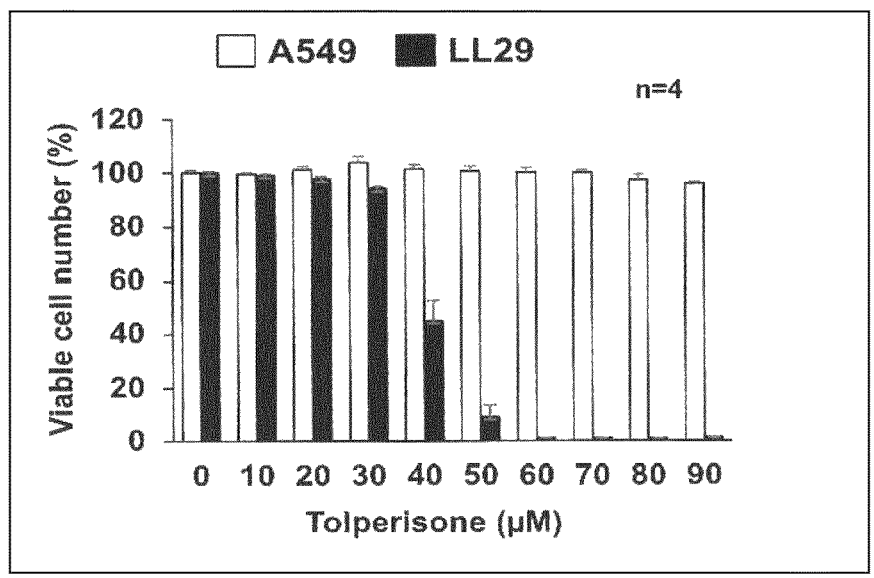
FIG. 9A shows actions of tolperisoneon on the survival cell number (%) of LL29 cell and A549 cell.
Figure 9B:
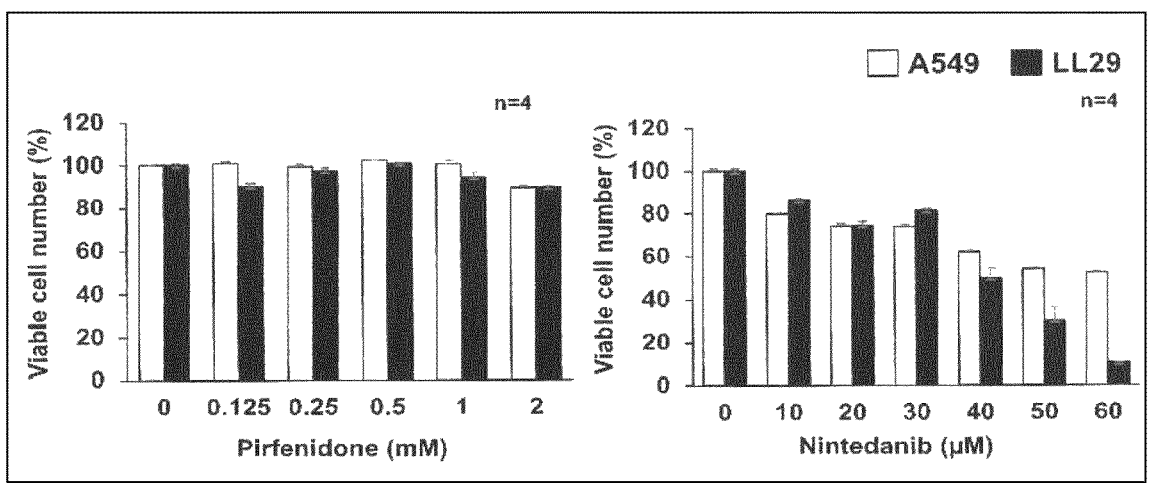
FIG. 9B shows actions of pirfenidone and nintedanib on the survival cell number of LL29 cell and A549 cell.

More dose patterns than those used during the screening test were applied to examine the cell death inducing action of tolperisone and to simultaneously conduct a screening reproducibility experiment. The results showed that tolperisone decreased the cell viability of LL29 cells (lung fibroblast cells) at a concentration lower than a concentration at which the cell viability of A549 cells (alveolar epithelial cells) decreased (FIG. 9A). Next, fibroblast cell-selective cell death was examined by using pirfenidone and nintedanib which are existing therapeutic drugs for IPF was examined, and the results showed that these two drugs hardly induced fibroblast cell-selective cell death (FIG. 9B).

(2) Effect of Airway Administration of Tolperisone on BLM-Dependent Pulmonary Fibrosing The therapeutic effect of tolperisone on pulmonary fibrosing was examined by using a BLM pulmonary injury model.

Figure 10A:
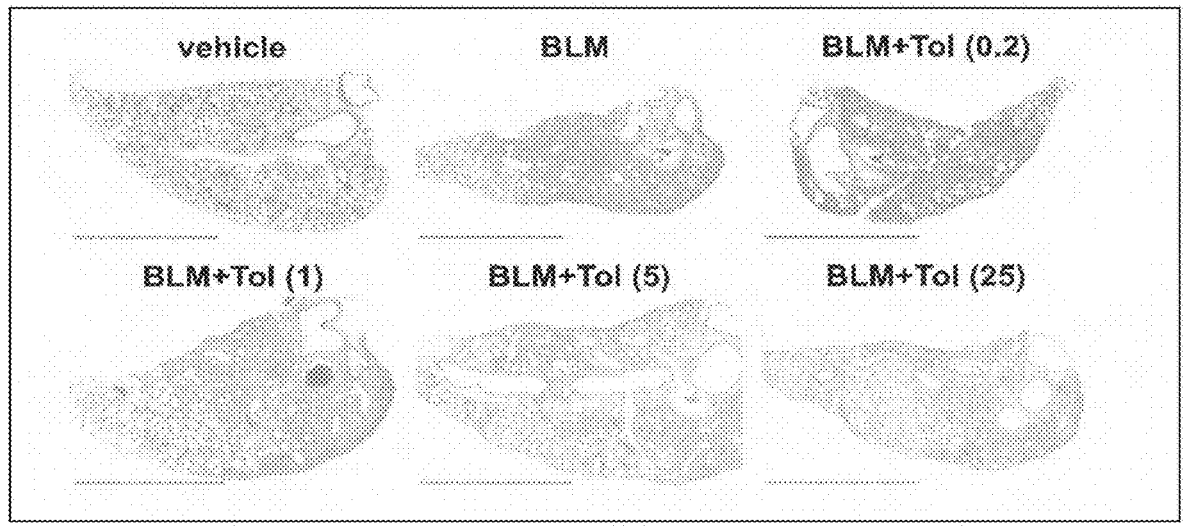
FIG. 10A shows an action of tolperisone (Tol) on BLM-Dependent Pulmonary fibrosing (collagen staining).
Figure 10B:
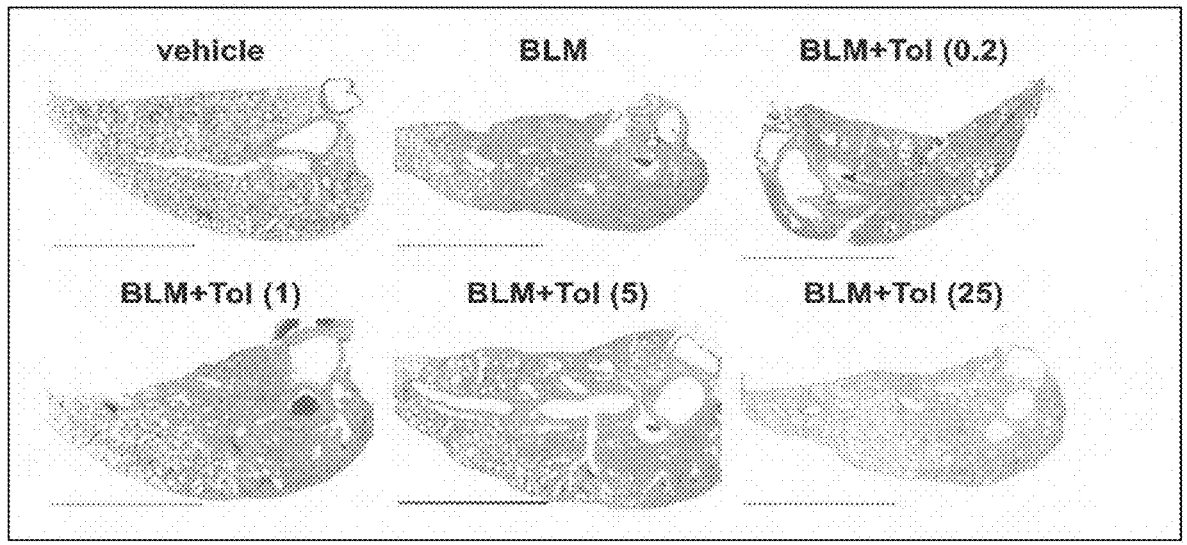
FIG. 10B shows an action of tolperisone on BLM-Dependent Pulmonary fibrosing (collagen staining).
Figure 10C:
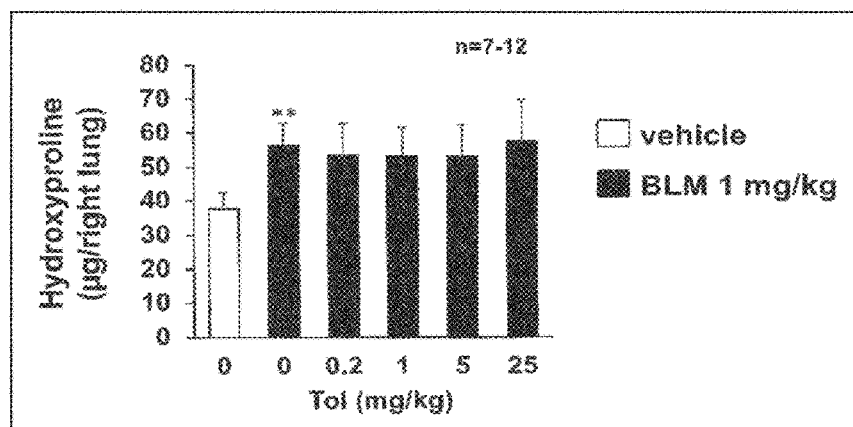
FIG. 10C shows an action of tolperisone on BLM-dependent pulmonary fibrosing (hydroxyproline amount).
Figure 10D:
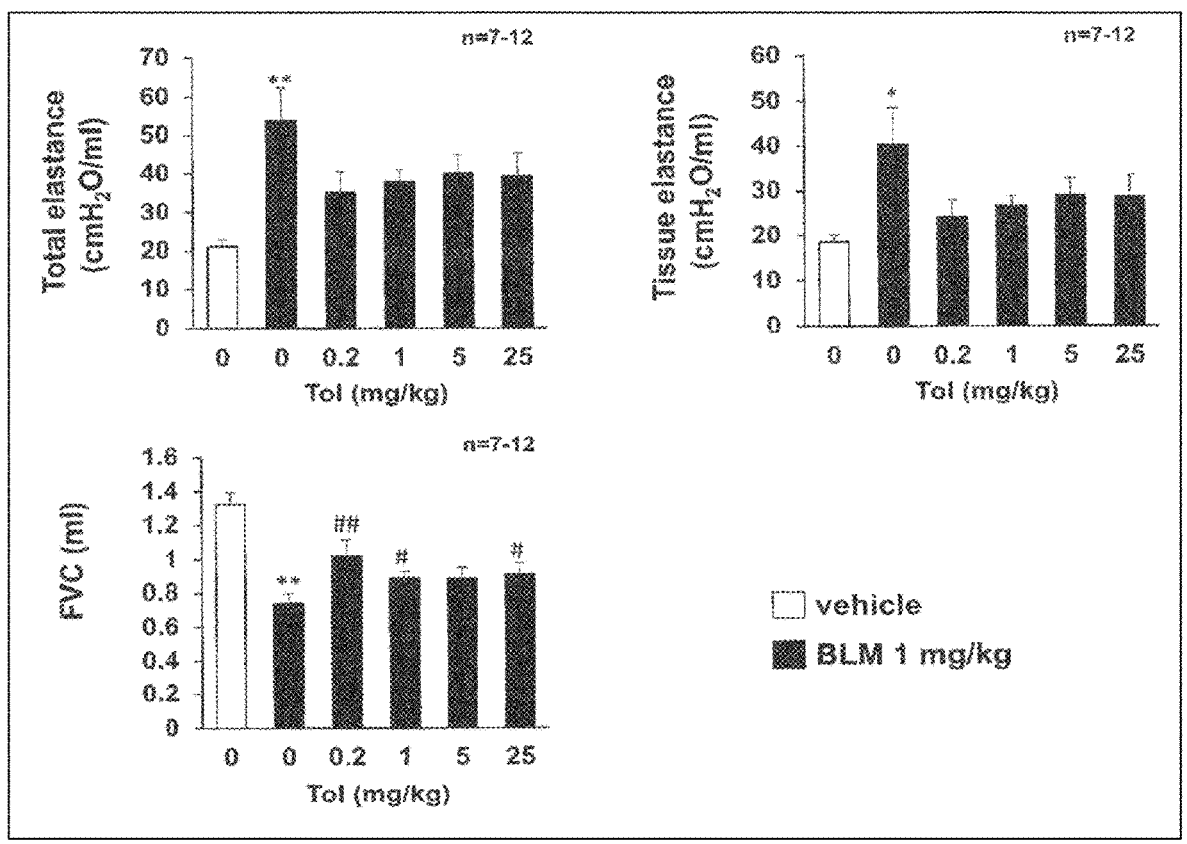
FIG. 10D shows an action of tolperisone on BLM-dependent pulmonary fibrosing (total lung and bronchi elastance, FVC).

BLM was administered via the airway to a mouse, and collagen was stained by H&E staining and Masson's trichrome staining, and it was confirmed that pulmonary injuries (thickening, and edemas of alveolar walls and stroma) and collagen accumulation occurred in a BLM-dependent manner. Airway administration of tolperisone slightly suppressed such injuries and collagen accumulation (FIGS. 10A and 10B). Further, the effect of tolperisone on BLM-dependent pulmonary fibrosing was evaluated by using as an index the amount of hydroxyproline which is an amino acid contained abundantly in collagen of the lung. The amount of hydroxyproline increased in a BLM-dependent manner, and airway administration of tolperisone hardly suppressed such an increase (FIG. 10C). Next, the respiratory function was measured by using a ventilator for mice. Administration of BLM increased the total respiratory system elastance (elastance of the total lung including bronchi, small bronchi and alveolus) and the tissue elastance (alveolar elastance), and airway administration of tolperisone tended to suppress such an increase (FIG. 10D). FVC decreased in a BLM-dependent manner, and airway administration of tolperisone suppressed such a decrease (FIG. 10D). The above results showed that airway administration of tolperisone suppressed BLM-dependent pulmonary fibrosing and a BLM-dependent decrease in respiratory function.

(3) Effect of Oral Administration of Tolperisone on BLM-Dependent Fibrosing

Figure 11A:
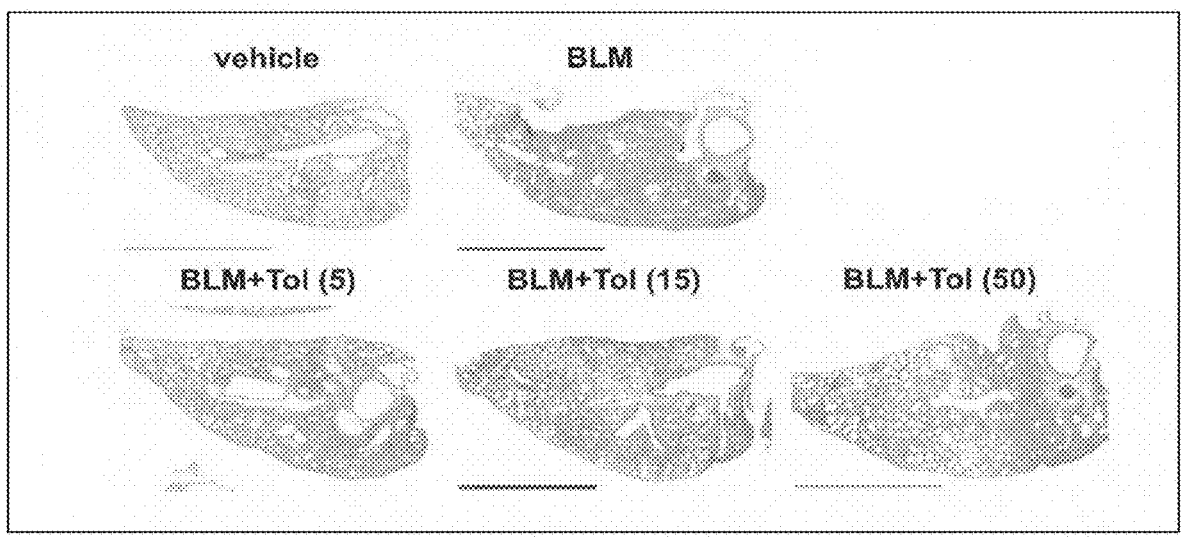
FIG. 11A shows an action of tolperisone on BLM-dependent pulmonary fibrosing (collagen staining).
Figure 11B:
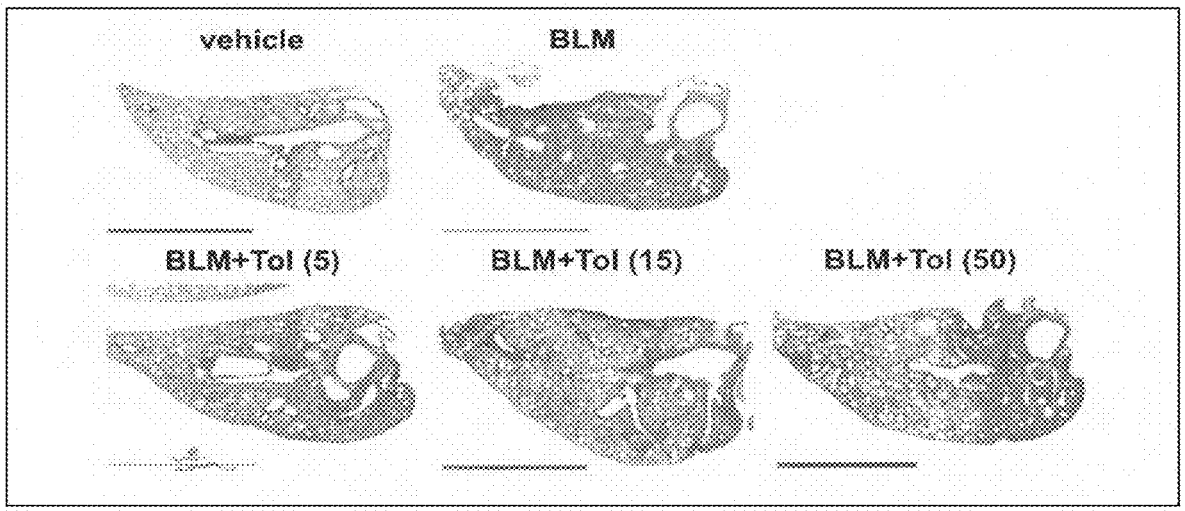
FIG. 11B shows an action of tolperisone (Tol) on BLM-dependent pulmonary fibrosing (collagen staining).
Figure 11C:
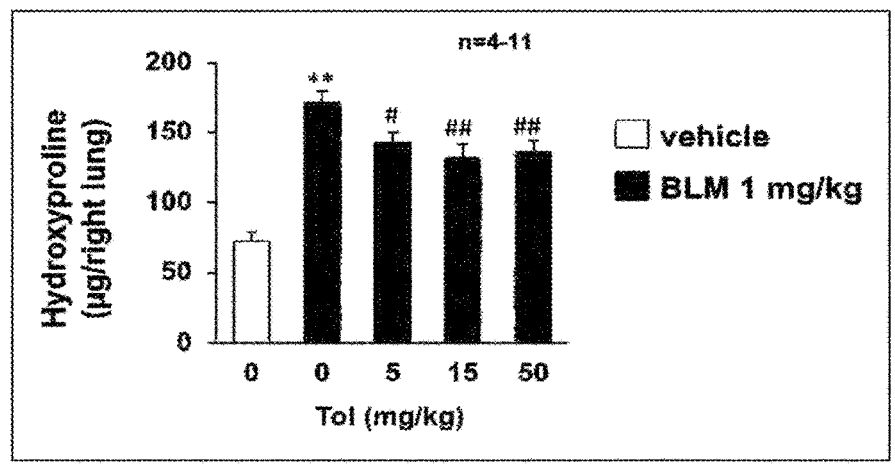
FIG. 11C shows an action of tolperisone (Tol) on BLM-dependent pulmonary fibrosing (hydroxyproline amount).
Figure 11D:
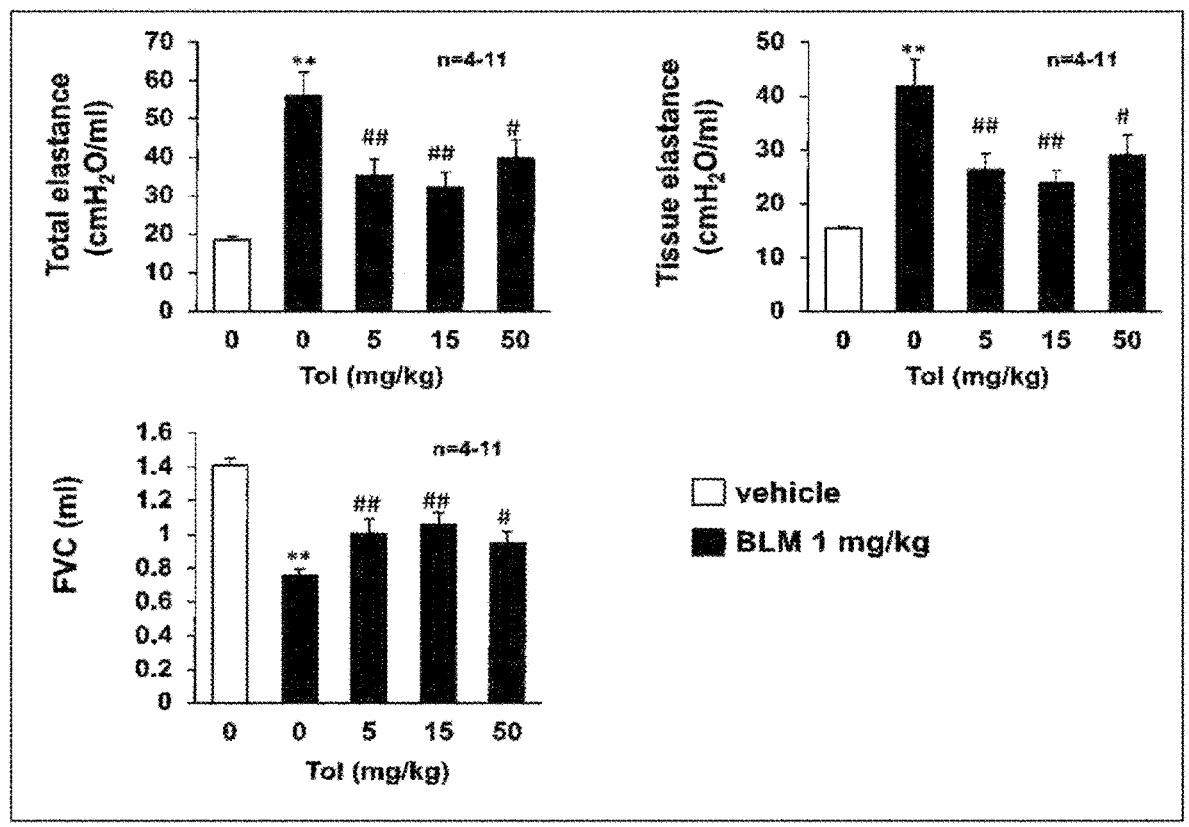
FIG. 11D shows an action of tolperisone (Tol) on BLM-dependent pulmonary fibrosing (total lung and bronchi elastance, FVC).

BLM was administered via the airway to a mouse, and collagen was stained by H&E staining and Masson's trichrome staining, and it was confirmed that pulmonary injuries (thickening, and edemas of alveolar walls and stroma) and collagen accumulation occurred in a BLM-dependent manner. Oral administration of tolperisone suppressed such injuries and collagen accumulation (FIGS. 11A and 11B). The amount of hydroxyproline increased in a BLM-dependent manner, and oral administration of tolperisone markedly suppressed such an increase (FIG. 11C). Next, the respiratory function was measured by using a ventilator for mice. Administration of BLM increased the total respiratory system elastance (elastance of the total lung including bronchi, small bronchi and alveolus) and the tissue elastance (alveolar elastance), and administration of tolperisone suppressed such an increase (FIG. 11D). FVC decreased in a BLM-dependent manner, and administration of tolperisone suppressed such a decrease (FIG. 11D). The above results showed that oral administration of tolperisone suppressed BLM-dependent pulmonary fibrosing and a BLM-dependent decrease in respiratory function.

Figure 12A:
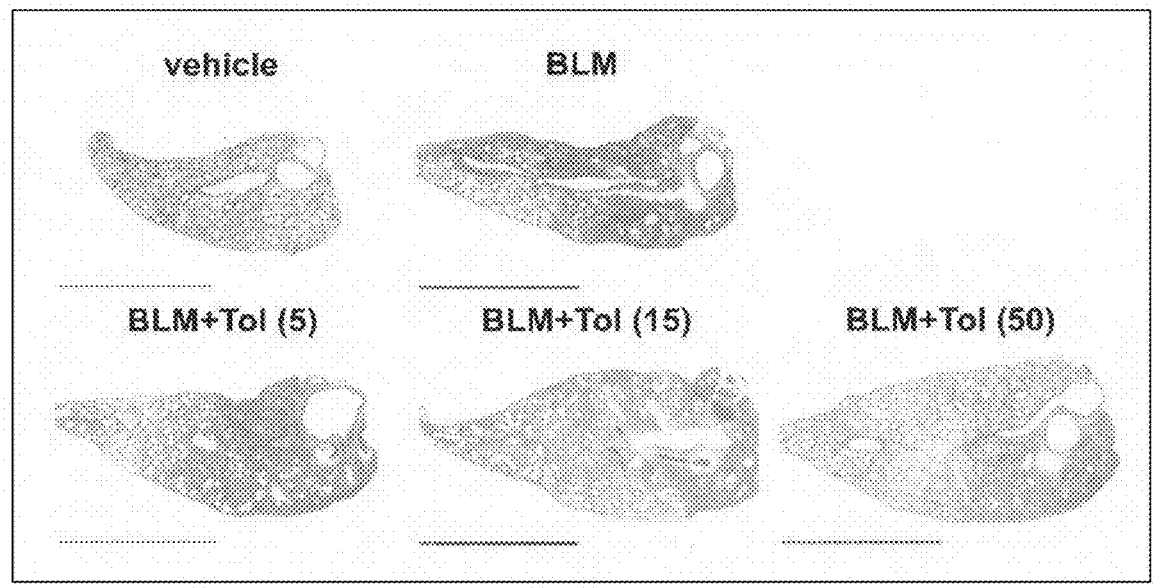
FIG. 12A shows a therapeutic effect of tolperisone (Tol) on BLM-dependent pulmonary fibrosing (collagen staining).
Figure 12B:
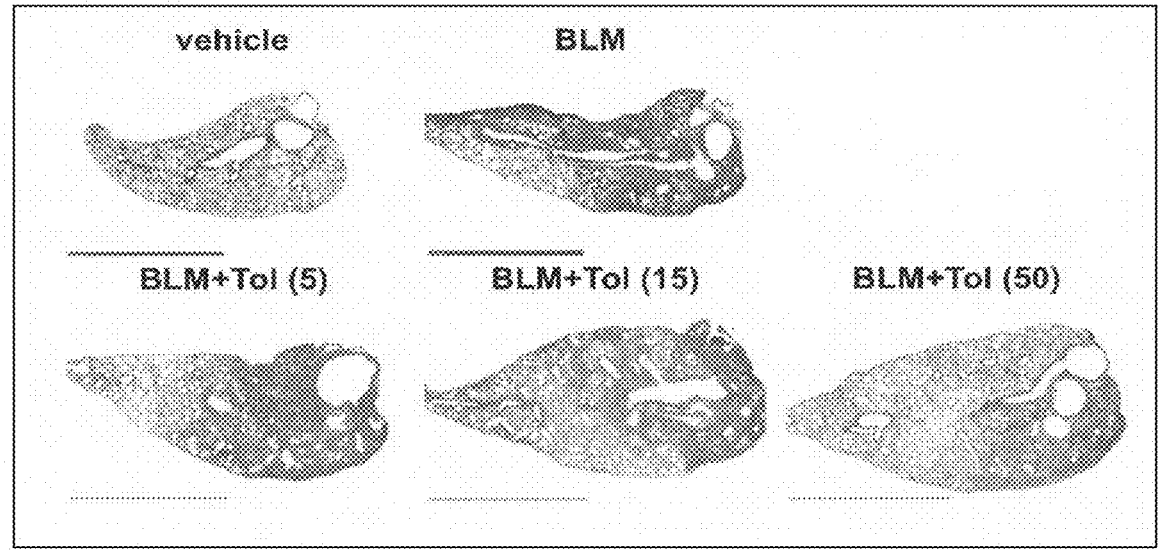
FIG. 12B shows a therapeutic effect of tolperisone (Tol) on BLM-dependent pulmonary fibrosing (collagen staining).
Figure 12C:
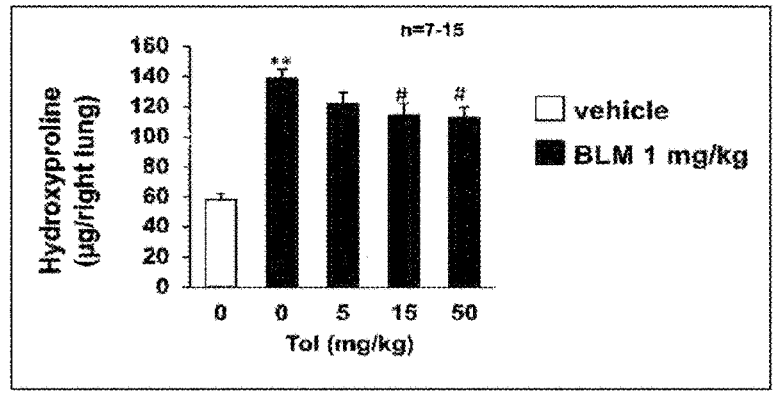
FIG. 12C shows a therapeutic effect of tolperisone (Tol) on BLM-dependent pulmonary fibrosing (hydroxyproline amount).

(4) Effect of Intraperitoneal Administration of Tolperisone on BLM-Dependent Pulmonary Fibrosing BLM was airway administered to a mouse, and collagen was stained by H&E staining and Masson's trichrome staining, and it was confirmed that pulmonary injuries (thickening, and edemas of alveolar walls and stroma) and collagen accumulation occurred in a BLM-dependent manner. Intraperitoneal administration of tolperisone suppressed such injuries and collagen accumulation (FIGS. 12A and 12B). The amount of hydroxyproline increased in a BLM-dependent manner, and intraperitoneal administration of tolperisone markedly suppressed such an increase (FIG. 12C).

Figure 12D:
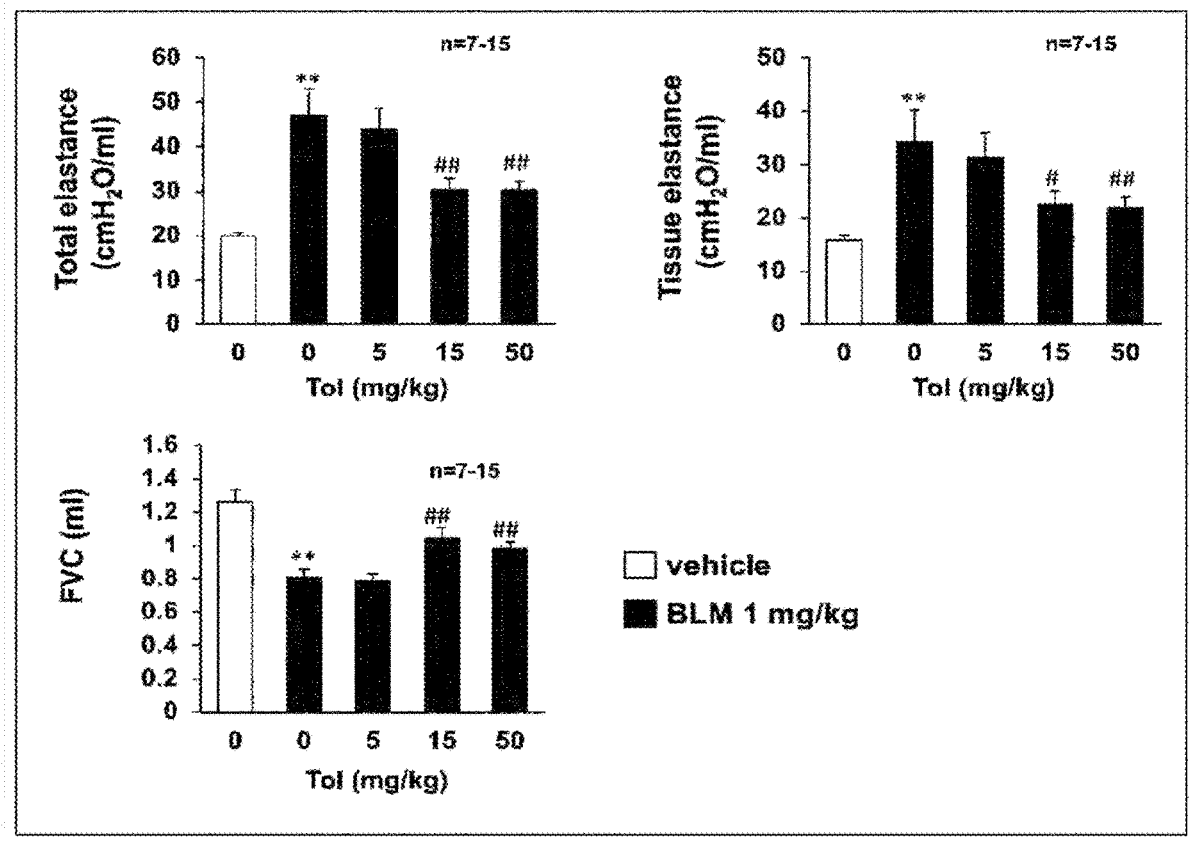
FIG. 12D shows a therapeutic effect of tolperisone on BLM-dependent pulmonary fiblosing (total lung and bronchi elastance, FVC).

Next, the respiratory function was measured by using a ventilator for mice. Administration of BLM increased the total respiratory system elastance (elastance of the total lung including bronchi, small bronchi and alveolus) and the tissue elastance (alveolar elastance), and administration of tolperisone suppressed such an increase (FIG. 12D). FVC decreased in a BLM-dependent manner, and administration of tolperisone suppressed such a decrease (FIG. 12D). The above results showed that intraperitoneal administration of tolperisone suppressed BLM-dependent pulmonary fibrosing and a BLM-dependent decrease in respiratory function.
(5) Effect of Drug of Same Type and Efficacy as Tolperisone (Selectivity on Fibroblast Cells)

Figure 13A:
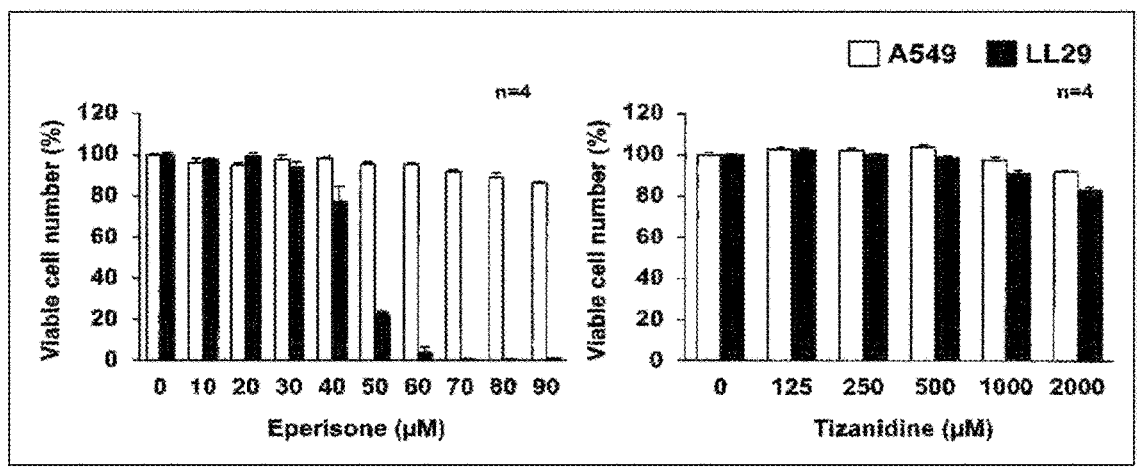
FIG. 13A shows actions of drugs with same indications (eperisone, tizanodine) on survival cell numbers (%) of LL29 cell and A549 cell.
Figure 13B:
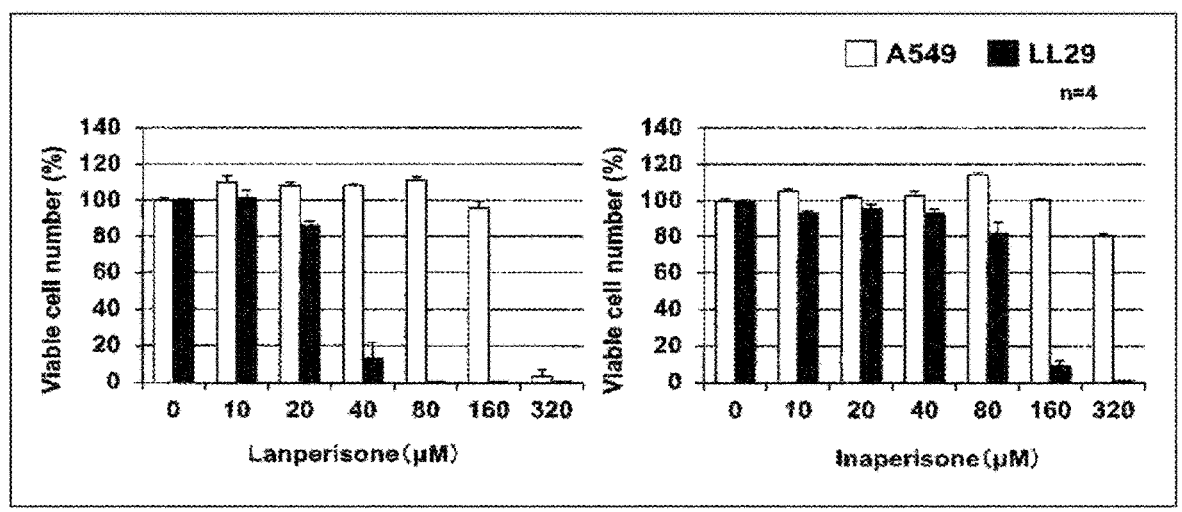
FIG. 13B shows actions of drugs with same indications (lanperisone, inaperisone) on survival cell number of LL29 cell and A549 cell.
Figure 14A:
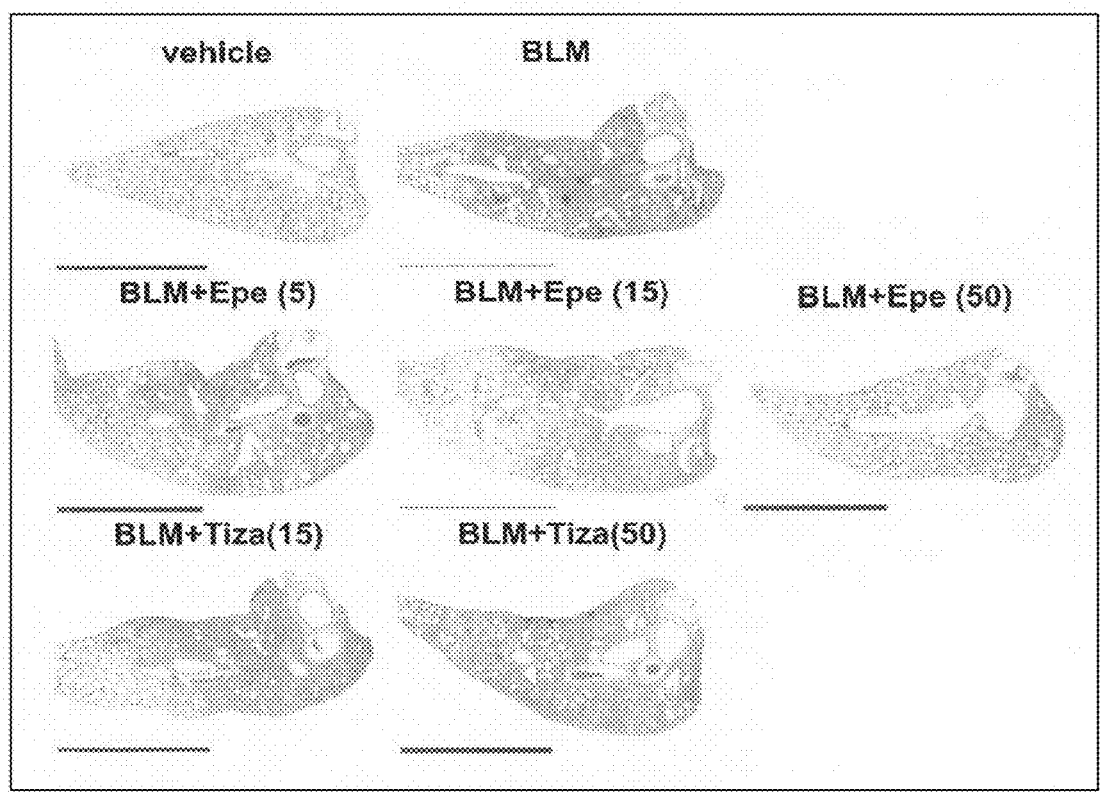
FIG. 14A shows actions of eperisone (Epe) and tizanidine (Tiza) on BLM-dependent pulmonary fiblosing (collagen staining).
Figure 14B:
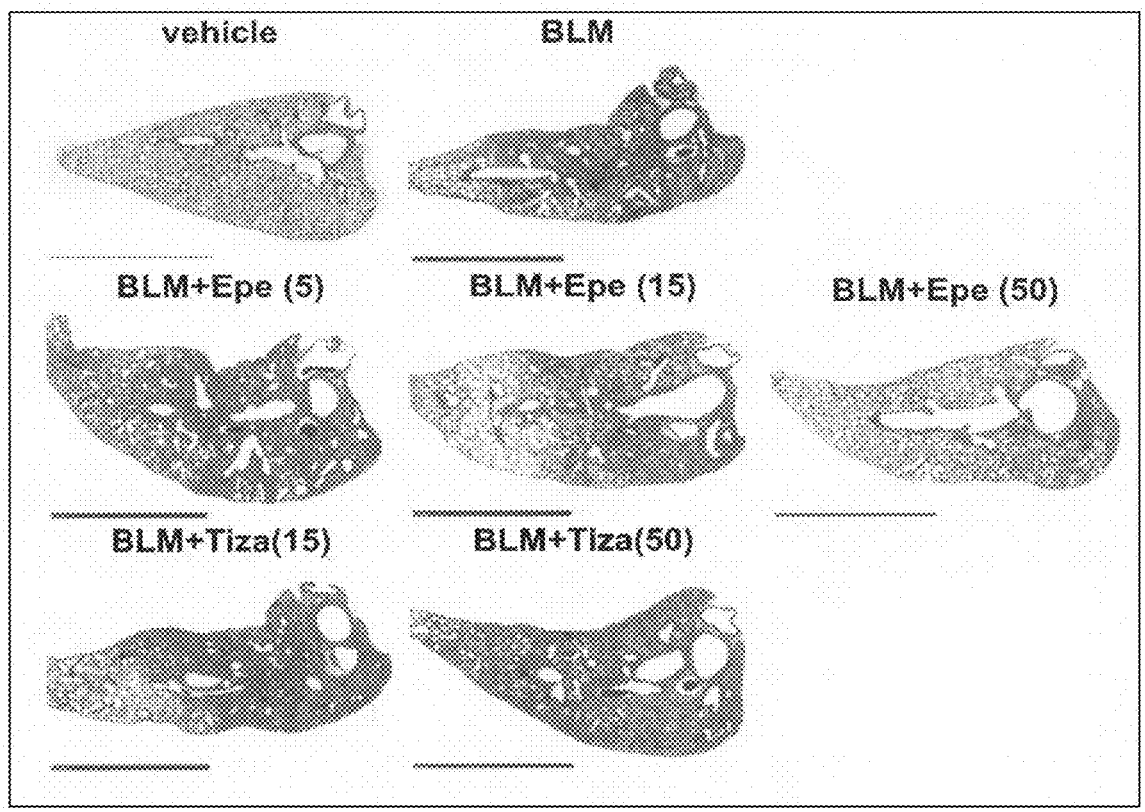
FIG. 14B shows actions of eperisone (Epe) and tizanidine (Tiza) on BLM-dependent pulmonary fiblosis (collagen staining).
Figure 14C:
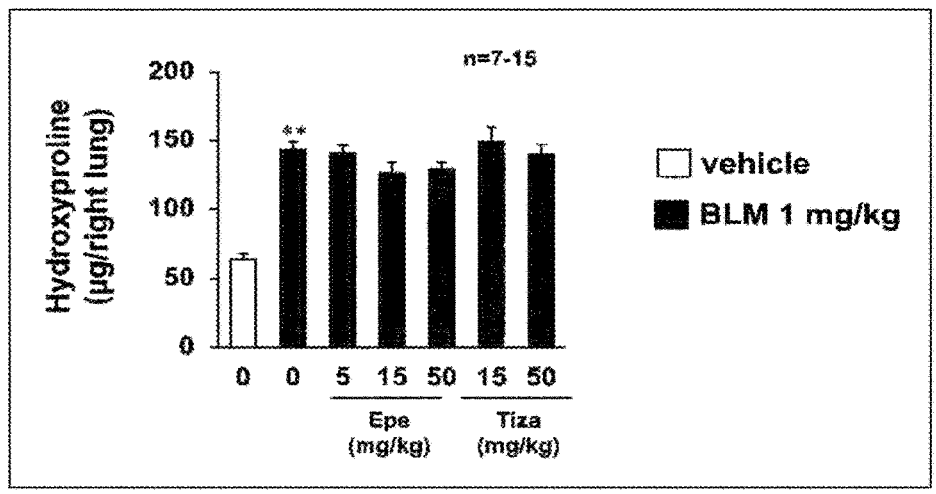
FIG. 14C shows actions of eperisone (Epe) and tizanidine (Tiza) on BLM-dependent pulmonary fiblosing (hydroxyproline amount).
Figure 14D:
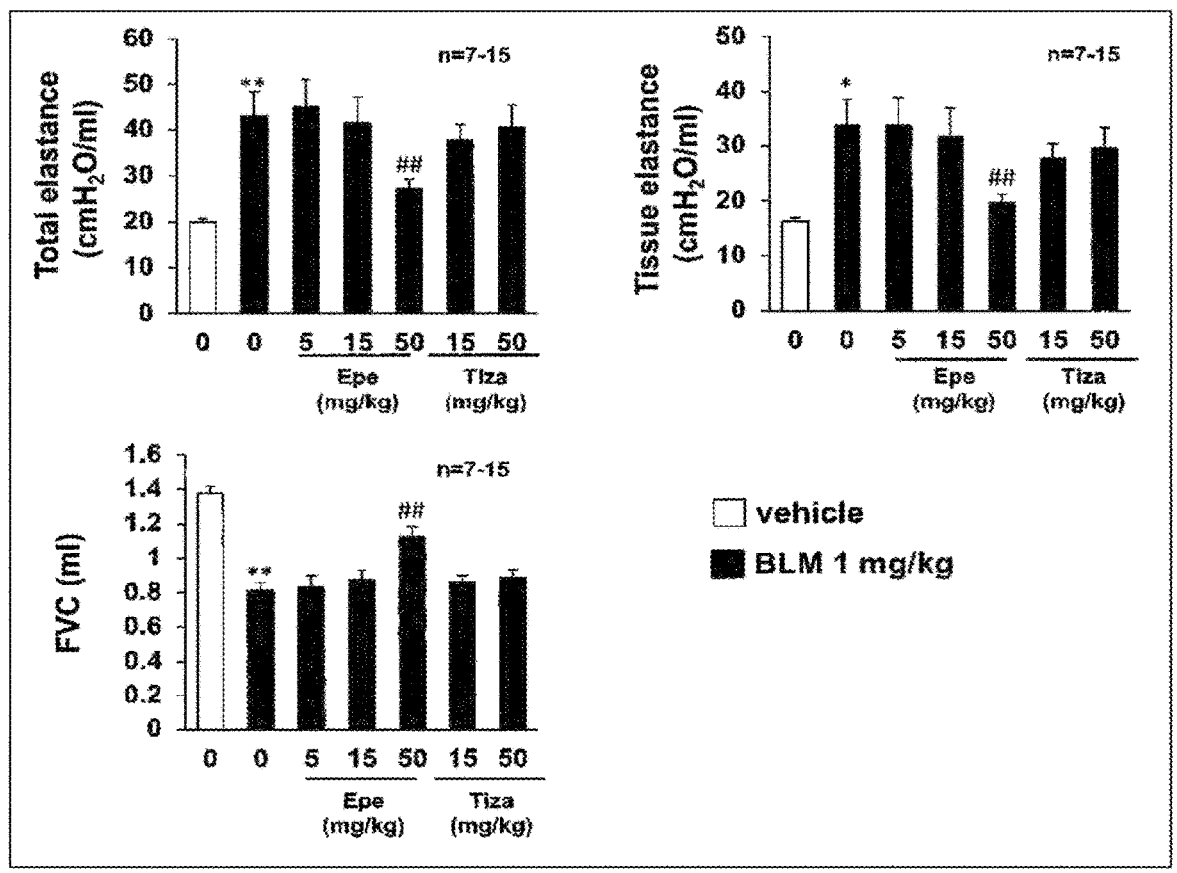
FIG. 14D shows an action of eperisone (Epe) and tizanidone (Tiza) on BLM-dependent pulmonary fiblosing (total lung and bronchi, FVC).
Figure 15:
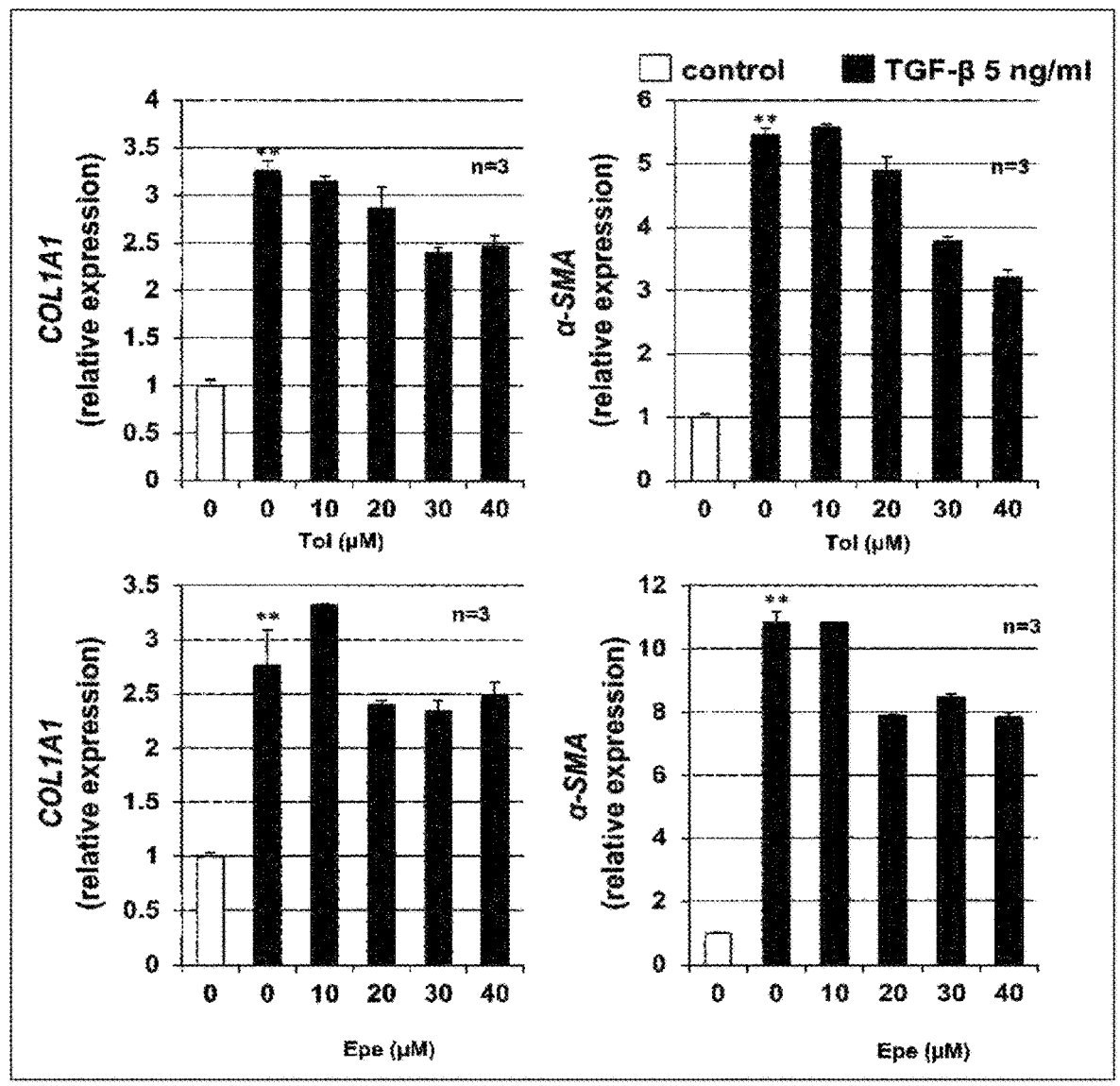
FIG. 15 shows actions of tolperisone (Tol) and eperisone (Epe) on α-SMA and COL1A1.

In FIG. 13, whether fibroblast cell-selective cell death occurred was analyzed by using drugs of the same type and efficacy in order to clarify a mechanism of selective action of tolperisone on fibroblast cells. The results showed that eperisone decreased the cell viability of LL29 cells at a concentration lower than a concentration at which the cell viability of A549 cells decreased, and tizanidine did not exhibit such an effect (FIG. 13A). Eperisone is a compound very similar in chemical structure to tolperisone. Thus, fibroblast cell-selectivity was analyzed by using a compound similar in chemical structure to tolperisone. The results showed that inaperisone and lanperisone, which are chemical-structural analogs to tolperisone, induced fibroblast cell-selective cell death similar to that induced by tolperisone (FIG. 13B).
(6) Effect of Intraperitoneal Administration of Eperisone and Tizanidine on BLM-Dependent Pulmonary Fibrosing BLM was administered to a mouse via the airway, and collagen was stained by H&E staining and Masson's trichrome staining. BLM-dependent pulmonary injury and collagen accumulation were suppressed by intraperitoneal administration of eperisone, but were not suppressed by intraperitoneal administration of tizanidine (FIGS. 14A and 14B). A tendency of suppression of the BLM-dependent amount of hydroxyproline by intraperitoneal administration of eperisone was observed, but such a tendency of suppression by intraperitoneal administration of tizanidine was not observed (FIG. 14C). Next, the respiratory function was measured by using a ventilator for mice. Administration of BLM increased the total respiratory system elastance (elastance of the total lung including bronchi, small bronchi and alveolus) and the tissue elastance (alveolar elastance), and decreased FVC. On the other hand, such reactions were suppressed by eperisone, but were not suppressed by tizanidine (FIG. 14D). The above results showed that like tolperisone, eperisone suppressed BLM-dependent pulmonary fibrosing and a decrease in respiratory function.
(7) Suppression of Activation of Fibroblast Cells by Tolperisone and Eperisone FIG. 15 shows the effects of tolperisone and eperisone on activation (an increase in levels of α-SMA and mRNA of collagen) of fibroblast cells treated with TGF-β1. Treatment of LL29 cells with TGF-β1 increased expression of α-SMA and Col1a1 mRNA, and treatment of LL29 cells with tolperisone and eperisone suppressed such induction. These results show that tolperisone and eperisone acted on fibroblast cells to suppress activation of lung fibroblast cells.
(8) Effects of Tolperisone and Existing Therapeutic Drugs for IPE on BLM-Dependent Pulmonary Fibrosing Pirfenidone and nintedanib are used as therapeutic drugs for IPF in clinical practice. Thus, tolperisone was compared with these drugs in terms of efficacy using BLM pulmonary injury models.

Bleomycin (BLM, 1 mg/kg) or a vehicle was administered to a mouse on day 0. Pirfenidone (200 mg/kg), nintedanib (30 mg/kg) or tolperisone (5 mg/kg) was orally administered to the mouse once a day for 9 days (from day 10 to day 18). 20 days later, a lung tissue section was prepared, and collagen was stained by H&E staining and Masson's trichrome staining.

Figure 16A:
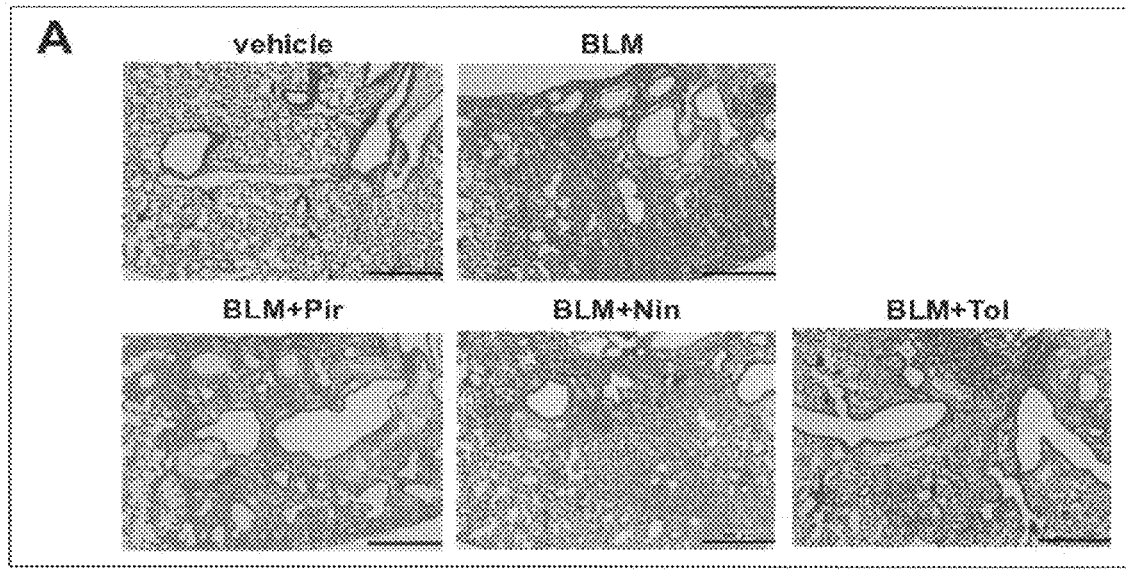
FIG. 16A shows therapeutic effects of tolperisone (Tok), pirfenidone (Pir) and nintedanib (Nin) on BLM-dependent pulmonary fiblosing (collagen staining).
Figure 16B:
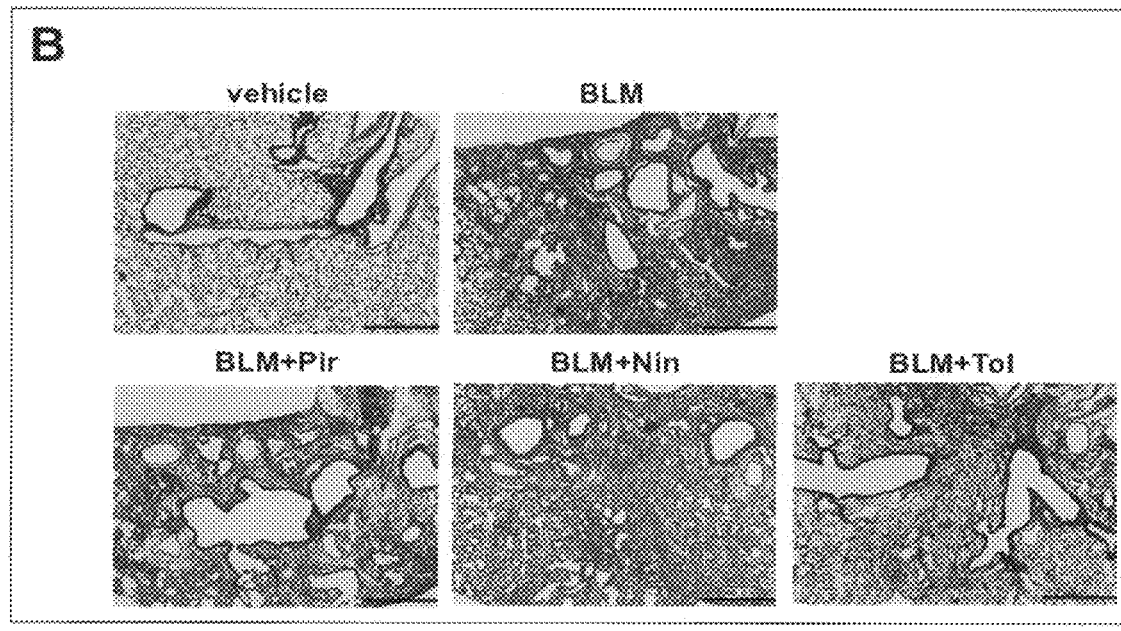
FIG. 16B shows therapeutic effects of tolperisone (Tok), pirfenidone (Pir) and nintedanib (Nin) on BLM-dependent pulmonary fiblosing.

The results showed that as shown in FIGS. 16A and 16B, pulmonary injuries (thickening, and edemas of alveolar walls and stroma) and collagen accumulation occurred in a BLM-dependent manner, and pirfenidone and nintedanib hardly suppressed BLM-dependent pulmonary injuries. In contrast, administration of tolperisone markedly improved BLM pulmonary injuries.

Figure 16C:
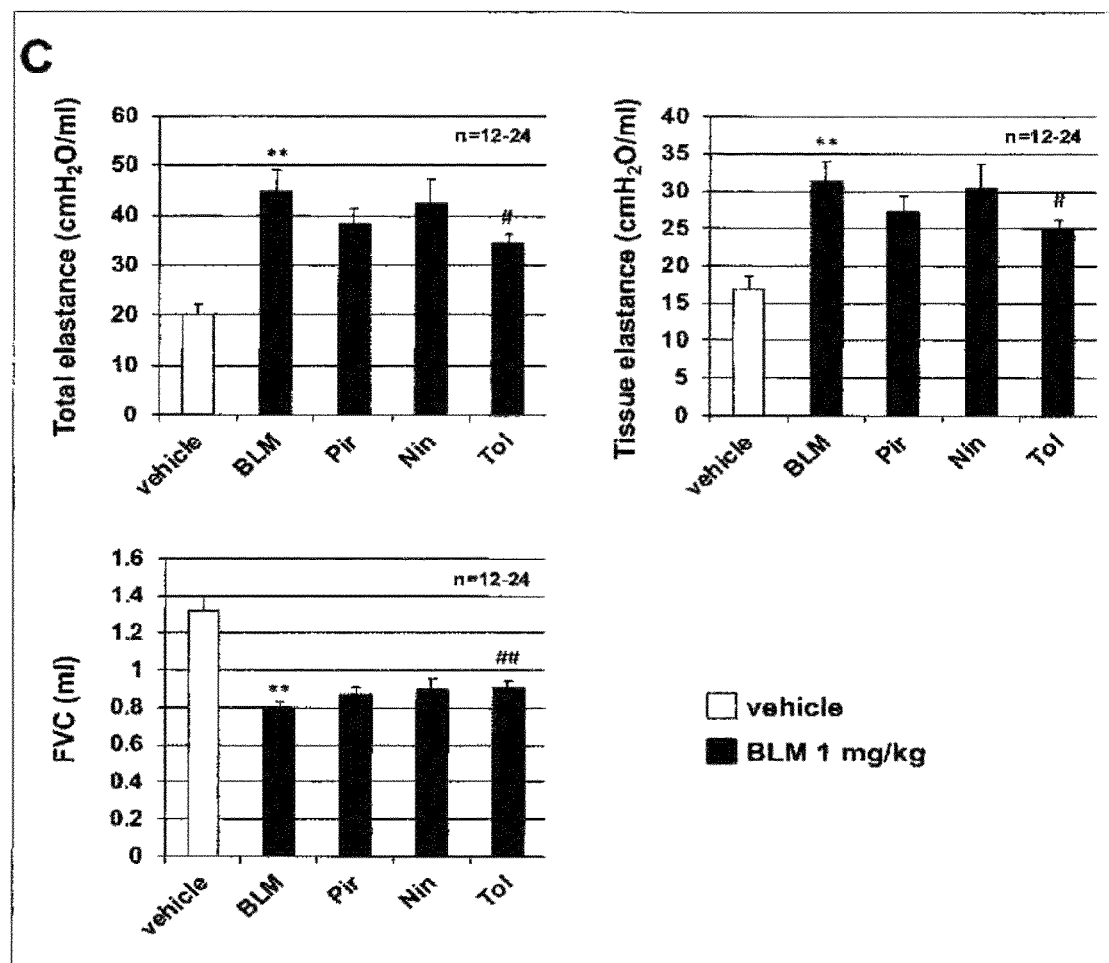
FIG. 16C shows therapeutic effects of tolperisone (Tol), pirfenidone (Pir) and nintedanib (Nin) on BLM-dependent lung fibrosing (total lung and bronchi elastance, FVC).

Next, the respiratory function was measured by using a ventilator for mice. The results showed that as shown in FIG. 16C, administration of BLM increased the total respiratory system elastance (elastance of the total lung including bronchi, small bronchi and alveolus) and the tissue elastance (alveolar elastance), and decreased FVC. Tolperisone improved such changes. To the contrary, two drugs other than tolperisone were unable to such changes. From the above results, tolperisone can be expected to have higher drug efficacy over existing therapeutic drugs for IPF.
(9) Effect of Oral Administration of Eperisone on BLM-Dependent Pulmonary Fibrosing In clinical practice, eperisone is used as a muscle tension improving drug for oral administration. Thus, the effect of oral administration was analyzed in addition to the foregoing intraperitoneal administration.

Figure 17A:
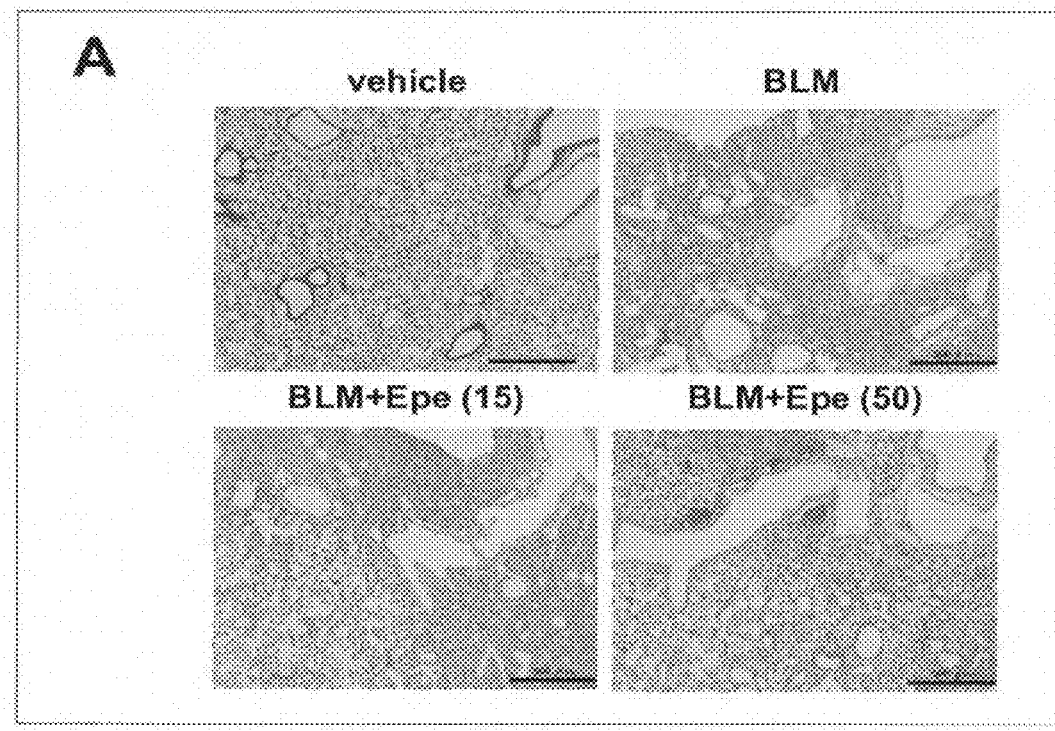
FIG. 17A shows a therapeutic effect of eperisone (Epe) on BLM-dependent pulmonary fiblosing (collagen staining).
Figure 17B:
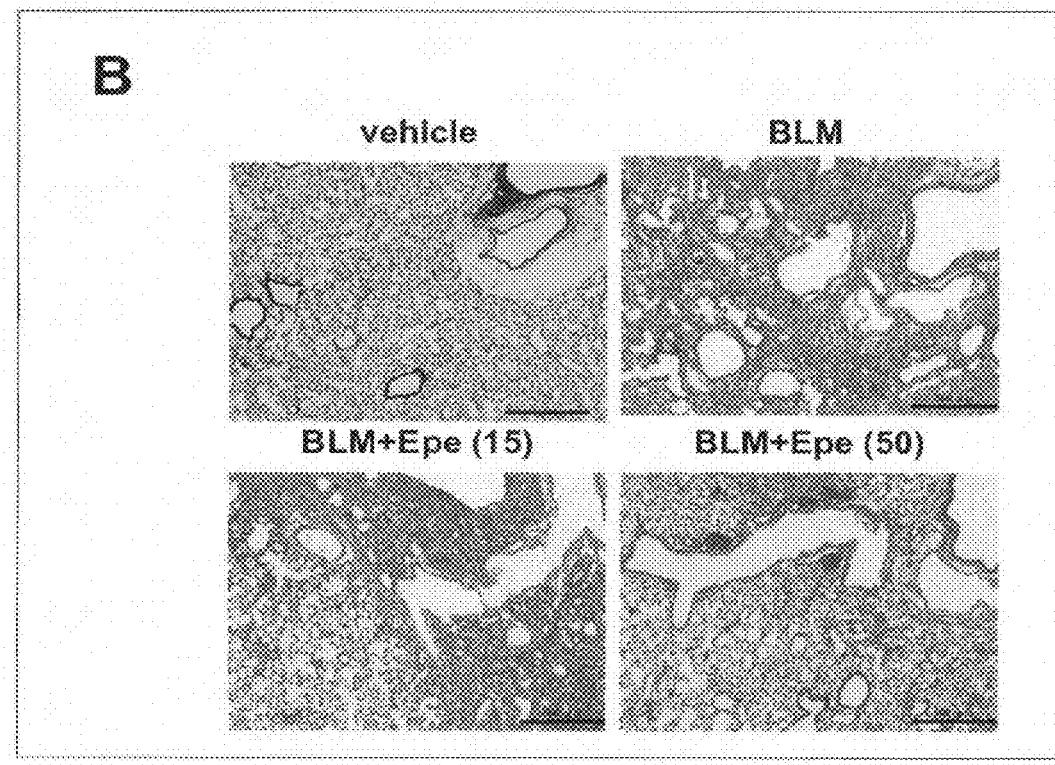
FIG. 17B shows a therapeutic effect of eperisone (Epe) on BLM-dependent pulmonary fibrosing (collagen staining).
Figure 17C:
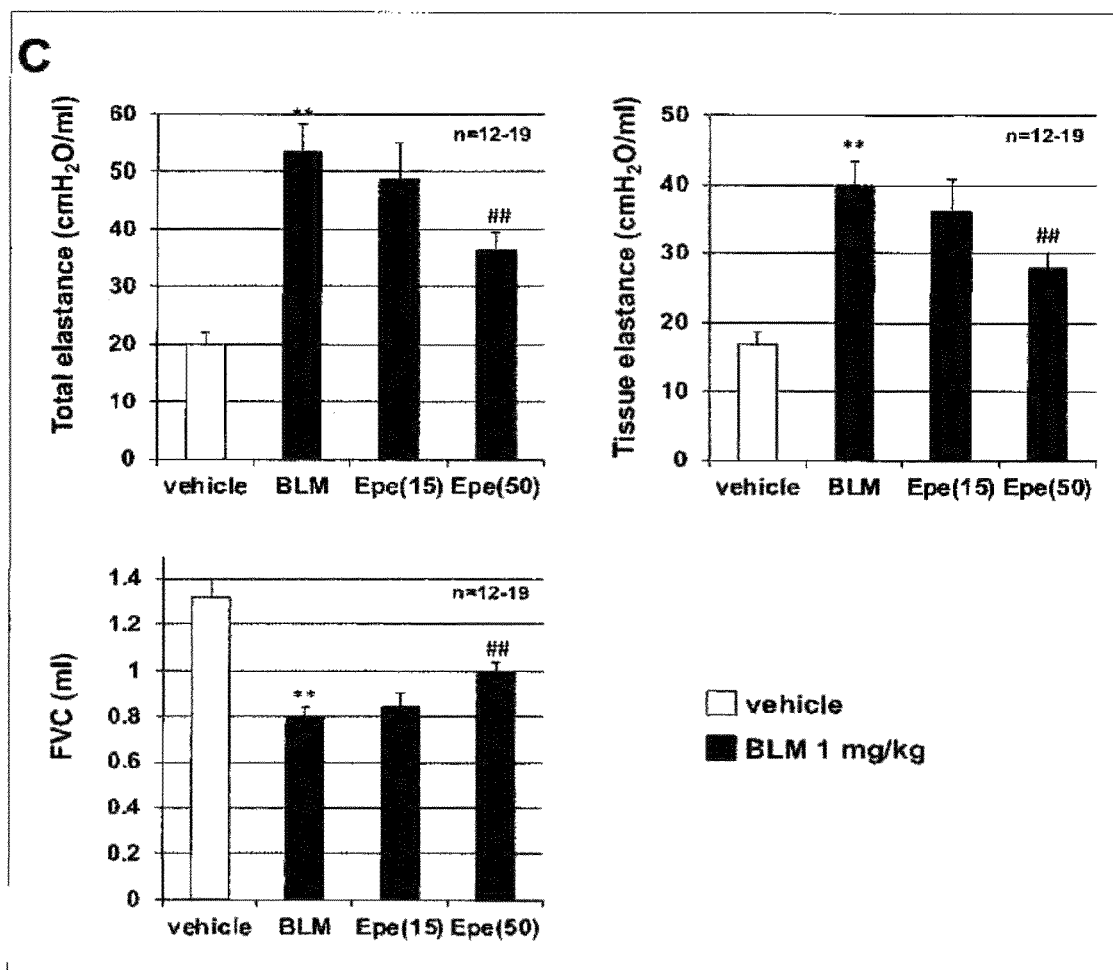
FIG. 17C shows a therapeutic effect of eperisone (Epe) on BLM-dependent pulmonary fiblosing (total lung and bronchi elastance, FVC).

Bleomycin (BLM, 1 mg/kg) or a vehicle was administered to a mouse on day 0. Eperisone (15 or 50 mg/kg) was orally administered to the mouse once a day for 9 days (from day 10 to day 18). 20 days later, a lung tissue section was prepared, and histological analysis was performed. Collagen was stained by H&E staining and Masson's trichrome staining. The results showed that as shown in FIGS. 17A and 17B, oral administration of eperisone suppressed BLM-dependent pulmonary injuries and collagen accumulation in a concentration-dependent manner. As shown in FIG. 17C, administration of BLM increased the total respiratory system elastance and the tissue elastance, and decreased FVC, and oral administration of eperisone improved such changes in a concentration-dependent manner. The above results show that eperisone has efficacy even in oral administration as a clinical administration method.

The invention claimed is:
1. A method for treating fibrosis, the method comprising administering to a subject in need thereof an effective amount of a compound of the following formula (I):

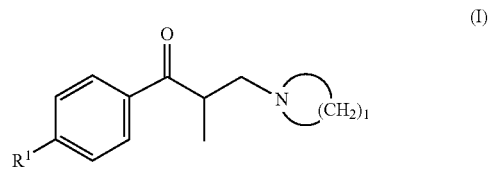

wherein R1 represents a C1-4 alkyl group optionally substituted with a halogen atom, and l represents an integer of 3 to 6,
or a pharmaceutically acceptable salt thereof or a solvate of the compound or the salt thereof,
wherein the fibrosis is idiopathic pulmonary fibrosis.

2. The method according to claim 1, wherein l is 4 or 5, and R1 is a methyl group, an ethyl group or a trifluoromethyl group.

3. The method according to claim 1, wherein l is 5, and R1 is a methyl group or an ethyl group.

4. The method according to claim 1, wherein the compound of the formula (I) is administered by airway administration.

5. The method according to claim 1, wherein the compound of the formula (I) is administered by oral administration.

6. The method according to claim 1, wherein the compound of the formula (I) is administered by transvenous administration.

* * * * *